US012584126B2

(12) United States Patent
Herzig et al.

(10) Patent No.: US 12,584,126 B2
(45) Date of Patent: Mar. 24, 2026

(54) microRNA INHIBITORS FOR USE IN TREATING METABOLIC DISEASES

(71) Applicant: Helmholtz Zentrum München Deutsches Forschungszentrum für Gesundheit und Umwelt (GmbH), Neuherberg (DE)

(72) Inventors: Stephan Herzig, Vaterstetten (DE); Manuel Gil Lozano, Unterschleissheim (DE); Tobias Schafmeier, Neubiberg (DE)

(73) Assignee: HELMHOLTZ ZENTRUM MUENCHEN—DEUTSCHES FORSCHUNGSZENTRUM FUER GESUNDHEIT UND UMWELT (GMBH) (DE)

( * ) Notice: Subject to any disclaimer, the term of this patent is extended or adjusted under 35 U.S.C. 154(b) by 898 days.

(21) Appl. No.: 17/251,803

(22) PCT Filed: Sep. 10, 2019

(86) PCT No.: PCT/EP2019/074056
§ 371 (c)(1),
(2) Date: Dec. 13, 2020

(87) PCT Pub. No.: WO2020/053186
PCT Pub. Date: Mar. 19, 2020

(65) Prior Publication Data
US 2021/0254067 A1     Aug. 19, 2021

(30) Foreign Application Priority Data
Sep. 11, 2018     (LU) .................................... LU100927

(51) Int. Cl.
*C12N 15/113*          (2010.01)
(52) U.S. Cl.
CPC ...... *C12N 15/113* (2013.01); *C12N 2310/113* (2013.01); *C12N 2310/13* (2013.01); *C12N 2320/31* (2013.01); *C12N 2320/32* (2013.01)
(58) Field of Classification Search
CPC ............ C12N 15/113; C12N 2310/113; C12N 2310/13; C12N 2320/31; C12N 2320/32
See application file for complete search history.

(56) References Cited

U.S. PATENT DOCUMENTS

| | | |
|---|---|---|
| 4,711,955 A | 12/1987 | Ward et al. |
| 5,525,711 A | 6/1996 | Hawkins et al. |
| 5,792,608 A | 8/1998 | Swaminathan et al. |

FOREIGN PATENT DOCUMENTS

| | | |
|---|---|---|
| EP | 0302175 A2 | 2/1989 |
| JP | 7530836 B2 | 8/2024 |
| WO | 2015063081 A2 | 5/2015 |

OTHER PUBLICATIONS

Broughton, James P et al. "Pairing beyond the Seed Supports MicroRNA Targeting Specificity." Molecular cell vol. 64,2 (2016): 320-333. doi:10.1016/j.molcel.2016.09.004 (Year: 2016).*
Choi, Cheolwon et al. "Effective experimental validation of miRNA targets using an improved linker reporter assay." Genetics research vol. 99 e2. Jan. 30, 2017, doi:10.1017/S001667231600015X (Year: 2017).*
Lima, Joana Filipa et al. "Anti-miRNA oligonucleotides: A comprehensive guide for design." RNA biology vol. 15,3 (2018): 338-352. doi: 10.1080/15476286.2018.1445959 (Year: 2018).*
Lv, Zhiyu et al. "miR-541-3p inhibits the viability and migration of vascular smooth muscle cells via targeting STIM1." Molecular medicine reports vol. 23,5 (2021): 312. doi:10.3892/mmr.2021.11951 (Year: 2021).*
Robertson B, Dalby AB, Karpilow J, Khvorova A, Leake D, Vermeulen A. Specificity and functionality of microRNA inhibitors. Silence. 2010;1(1):10. Published Apr. 1, 2010. doi:10.1186/1758-907X-1-10 (Year: 2010).*
Shiah, Shine-Gwo et al. "MIR-30a and miR-379 modulate retinoic acid pathway by targeting DNA methyltransferase 3B in oral cancer." Journal of biomedical science vol. 27,1 46. Apr. 2, 2020, doi: 10.1186/s12929-020-00644-z (Year: 2020).*
Wen D, Danquah M, Chaudhary AK, Mahato RI. Small molecules targeting microRNA for cancer therapy: Promises and obstacles. J Control Release. 2015;219:237-247. doi:10.1016/j.jconrel.2015.08.011 (Year: 2015).*
Xu, Li et al. "miR-541 suppresses proliferation and invasion of squamous cell lung carcinoma cell lines via directly targeting high-mobility group AT-hook 2." Cancer medicine vol. 7,6 (2018): 2581-2591. doi: 10.1002/cam4.1491 (Year: 2018).*
Zhao X, Chu J. MicroRNA-379 suppresses cell proliferation, migration and invasion in nasopharyngeal carcinoma by targeting tumor protein D52. Exp Ther Med. 2018; 16(2):1232-1240. doi:10.3892/etm.2018.6302 (Year: 2018).*

(Continued)

*Primary Examiner* — Jennifer Dunston
*Assistant Examiner* — Christina Tran
(74) *Attorney, Agent, or Firm* — Dilworth IP, LLC

(57) ABSTRACT

The present invention relates to composition comprising an inhibitor of miR-379 or a portion or fragment thereof and an inhibitor of miR-541 or a portion or fragment thereof, and/or an inhibitor of the target site of miR-379 or a portion or fragment thereof and an inhibitor of the target site of miR-541 or a portion or fragment thereof, and/or a combination of an inhibitor of miR-379 or a portion or fragment thereof and an inhibitor of the target site of miR-541 or a portion or fragment thereof or a combination of an inhibitor of the target site of miR-379 or a portion or fragment thereof and an inhibitor of miR-541 or a portion or fragment thereof. The present invention also relates to the respective composition for use in treating or preventing a metabolic disease, a disease related to a metabolic disorder, and/or cancer.

8 Claims, 14 Drawing Sheets

Figure 1:
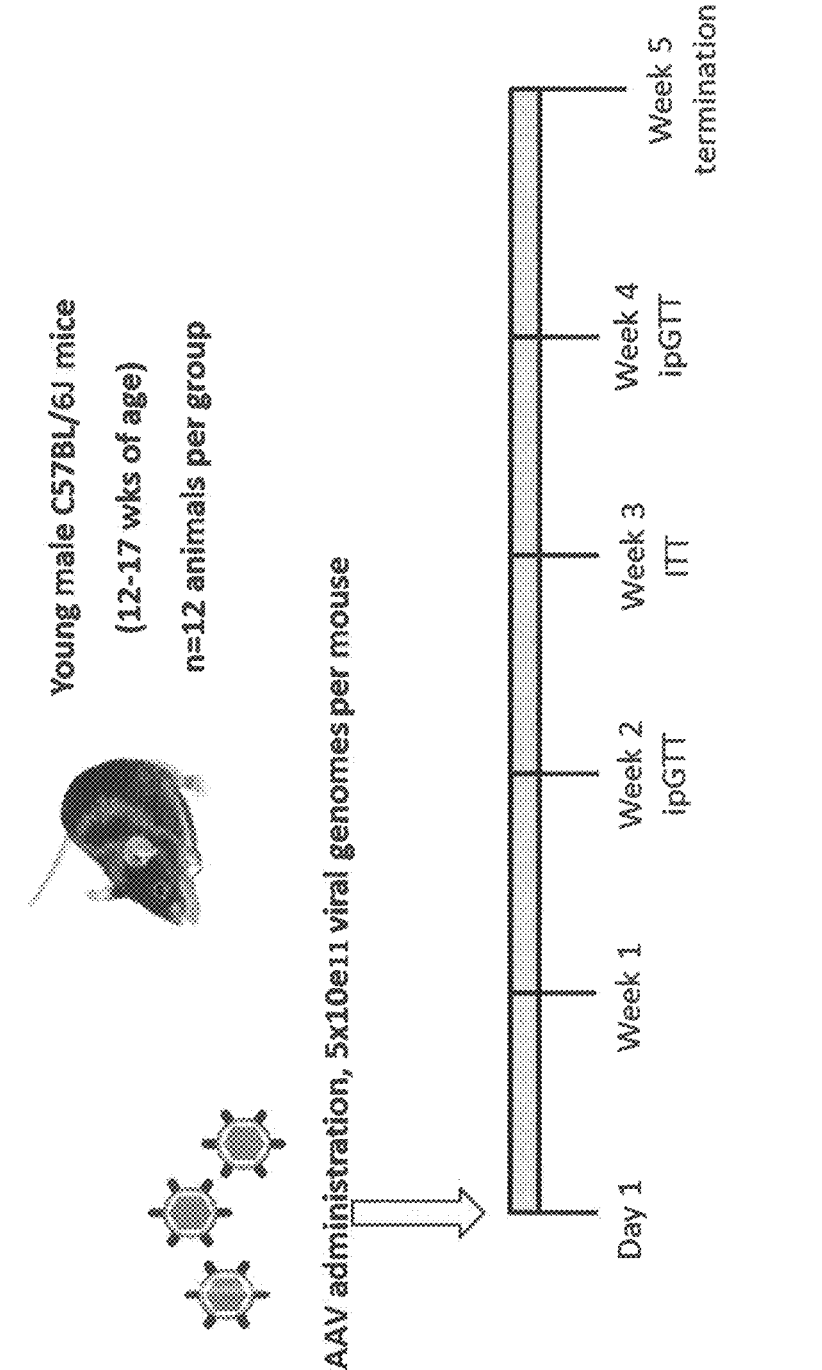

Specification includes a Sequence Listing.

(56) References Cited

OTHER PUBLICATIONS

Horwich, M. D., & Zamore, P. D. (2008). Design and delivery of antisense oligonucleotides to block microRNA function in cultured *Drosophila* and human cells. Nature protocols, 3(10), 1537-1549. (Year: 2008).*

Montgomery, R. L., Hullinger, T. G., Semus, H. M., Dickinson, B. A., Seto, A. G., Lynch, J. M., . . . & Van Rooij, E. (2011). Therapeutic inhibition of miR-208a improves cardiac function and survival during heart failure. Circulation, 124(14), 1537-1547. (Year: 2011).*

Rasmussen, S., Roberts, P. Functional studies of microRNA based on knockdown using Locked Nucleic Acid probes. Nat Methods 4, iii-iv (2007). https://doi.org/10.1038/nmeth1034 (Year: 2007).*

Zhou, J., Gregurick, S. K., Krueger, S., & Schwarz, F. P. (2006). Conformational changes in single-strand DNA as a function of temperature by SANS. Biophysical journal, 90(2), 544-551. (Year: 2006).*

Zhang, D. Y., Chen, S. X., & Yin, P. (2012). Optimizing the specificity of nucleic acid hybridization. Nature chemistry, 4(3), 208-214. (Year: 2012).*

Notice of Reasons for Rejection issued in Japanese Patent Application No. 2020-569736, issued Mar. 16, 2023, 6 pages.

Liu, F., Li, N., Long, B. et al. Cardiac hypertrophy is negatively regulated by miR-541. Cell Death Dis 5, e1171 (2014).

De Guia et al., microRNA-379 couples glucocorticoid hormones to dysfunctional lipid homeostasis. EMBO J. Feb. 3, 2015;34(3):344-60. doi: 10.15252/embj.201490464. Epub Dec. 15, 2014. PMID: 25510864; PMCID: PMC4339121.

Gururajan M, Josson S, Chu GC, et al. miR-154* and miR-379 in the DLK1-DIO3 microRNA mega-cluster regulate epithelial to mesenchymal transition and bone metastasis of prostate cancer. Clin Cancer Res. 2014;20 (24):6559-6569.

International Search Report issued in International Application No. PCT/EP2019/074056, Issued Dec. 20, 2019, 3 pages.

Rose, Adam J. et al., Molecular Control of Systemic Bile Acid Homeostasis by the Liver Glucocorticoid Receptor, Cell Press, Cell Metabolism 14, Jul. 6, 2011, Elsevier Inc. pp. 123-130.

Gamper, Howard B. et al., The DNA strand of chimeric RNA/DNA oligonucleotides can direct gene repair/conversion activity in mammalian and plant cell-free extracts, Nucleic Acids Research, 2000, vol. 28, No. 21, pp. 4332-4339.

Decision of Rejection received for Japanese Application No. 2024-037853, mailed on Nov. 20, 2025, 7 pages (4 pages of English Translation and 3 pages of Original Document).

* cited by examiner

A

B

A

B

C

A

B

C microRNA INHIBITORS FOR USE IN TREATING METABOLIC DISEASES

SEQUENCE LISTING

The instant application contains a Sequence Listing which is being submitted electronically in CRF format, created on Mar. 25, 2025, named 298-012US_ST25.txt and is 2,176 bytes in size.

The present invention relates to a composition comprising an inhibitor of miR-379 or a portion or fragment thereof and an inhibitor of miR-541 or a portion or fragment thereof, and/or an inhibitor of the target site of miR-379 or a portion or fragment thereof and an inhibitor of the target site of miR-541 or a portion or fragment thereof, and/or a combination of an inhibitor of miR-379 or a portion or fragment thereof and an inhibitor of the target site of miR-541 or a portion or fragment thereof or a combination of an inhibitor of the target site of miR-379 or a portion or fragment thereof and an inhibitor of miR-541 or a portion or fragment thereof. The present invention further relates to such compositions for use in treating or preventing a metabolic disease, a disease related to a metabolic disorder, and/or cancer.

Metabolic dysfunctions and diseases are often associated with a disbalanced level of glucocorticoid hormones and are associated with conditions such as, e.g., fasting, cancer cachexia, aging, Cushing's syndrome, GC therapy, obesity, insulin resistance, diabetes type 1 and 2, hyperglycemia, dyslipidemia, HCC (hepatocellular cancer), and others. For example, the metabolic syndrome (a constellation of metabolic disorders that all result from, or are associated with, a primary disorder of insulin resistance) is characterized by a group of metabolic risk factors including abdominal obesity, elevated triglyceride levels, decreased high density lipoprotein (HDL) cholesterol levels, high blood pressure, and impaired fasting blood glucose (a measure for decreased insulin sensitivity and increased risk of developing diabetes). Patients suffering from such conditions and diseases are at increased risk of coronary heart disease and other atherosclerotic conditions such as stroke and peripheral vascular disease and diabetes type 2.

The hypothalamic-pituitary-adrenal (HPA) endocrine axis is a critical physiological stress circuit to maintain body homeostasis during diverse situations such as trauma, exercise or nutrient deprivation. In metabolic control, GC signaling acts as a major counter-regulatory system against insulin action, and aberrantly elevated GC activity is tightly linked to major components of the Metabolic Syndrome, including obesity, insulin resistance, hyperglycemia, and systemic dyslipidemia. Indeed, GC levels have been found to be elevated in insulin-resistant patients and are strongly associated with a hyperglycemic and fatty liver phenotype, mediated through the glucocorticoid receptor (GR), a member of the nuclear receptor transcription factor family. In congruence, obesity is characterized by enhanced local GC action, and states of either endogenous or exogenous GC deficiency or excess, e.g. Addison's disease, Cushing's syndrome, or GC therapy, respectively, are characterized by severe perturbations in systemic energy metabolism that closely mimic aspects of the Metabolic Syndrome.

A class of small non-coding RNAs (microRNAs, also referred to herein as miRNAs or miRs) has emerged as a critical layer of metabolic control. MicroRNAs (miRNAs, miRs) are a class of small (e.g., 18-24 nucleotides) non-coding RNAs that exist in a variety of organisms, including mammals, and are conserved in evolution. miRNAs are processed from hairpin precursors of about 70 nucleotides, which are derived from primary transcripts through sequential cleavage by RNAse III enzymes. Many microRNAs can be encoded in intergenic regions, hosted within introns of pre-mRNAs or within non-coding RNA genes. Many miR-NAs also tend to be clustered and transcribed as polycistrons and often have similar spatial temporal expression patterns. miRs have been found to have roles in a variety of biological processes including developmental timing, differentiation, apoptosis, cell proliferation, organ development, and metabolism. Indeed, individual miRNA have been found to regulate diverse aspects of energy homeostasis, including pancreatic beta cell insulin secretion, adipose tissue lipid storage, and hepatic cholesterol and lipid handling. Also, some miRNAs such as miR-379 have been identified to be involved in glucocorticoid (GC) signaling (WO 2015/063081). For example, inhibition of miR-379 activity was shown to lower circulating triglyceride (TG) levels (de Guia et al., EMBO J (2015), 34 (3): 344-360). However, metabolic dysfunctions and diseases are still not yet treatable in a sufficient manner and suitable therapies for such diseases including diabetes type 1 and 2 are desirable.

The present invention addresses these needs and objectives by providing solutions as described herein and as defined in the claims.

As shown before in animal studies, inhibition of miR-379 activity leads to lower circulating triglyceride (TG) levels (de Guia et al., EMBO J (2015), 34 (3): 344-360). As has further been found in context with the present invention, another miRNA, i.e. miRNA-541 (miR-541), was found to be overexpressed in obese patients, identifying a correlation of miR-541 with insulin sensitivity (cf. Table 1). However, inhibition or knock-down of miR-541 did not lead to a substantial metabolic phenotype (data not shown). Yet, as has surprisingly been found in context with the present invention and shown herein, simultaneous inhibition of both, miR-379 and miR-541 improves both, glucose and lipid metabolism by lowering TG and glucose levels. This surprising finding leads to the current invention where both, miR-379 and miR-541 are inhibited, allowing treatment of disorders and diseases correlated with glucose and lipid metabolism, including, but not limited to, glucocorticoid hormone driven metabolic dysfunction, obesity, diabetes (including type 1 and 2), diabesity, metabolic syndrome, insulin resistance, hyperglycemia, (systemic) dyslipidemia, Cushing's syndrome, adverse or side effects associated with or caused by glucocorticoid (GC) treatment or excess, atherosclerosis, heart disease, stroke, (cancer) cachexia, and growth defects, hepatic steatosis, NASH, and liver fibrosis, particularly diabetes type 1 and 2, including personalized treatment of diabetes type 1 and 2.

Thus, the present invention relates to a composition comprising (a) an inhibitor of miR-379 or a portion or fragment thereof and an inhibitor of miR-541 or a portion or fragment thereof, and/or (b) an inhibitor of the target site of miR-379 or a portion or fragment thereof and an inhibitor of the target site of miR-541 or a portion or fragment thereof, and/or (c) a combination of an inhibitor of miR-379 or a portion or fragment thereof and an inhibitor of the target site of miR-541 or a portion or fragment thereof or a combination of an inhibitor of the target site of miR-379 or a portion or fragment thereof and an inhibitor of miR-541 or a portion or fragment thereof.

As used herein, the term "target site" is the site within mRNA of a cell, which is normally targeted by the miRNA in order to suppress or inhibit translation of that mRNA, to allow cleavage of that mRNA, or to destabilize that mRNA to allow accelerated degradation (also known to the skilled person as "silencing" of the mRNA). Consequently, the term "inhibitor of the target site" means in the context of the present invention an inhibitor of such "target site" as defined above. Thus, the composition as described and provided in context with the present invention may comprise an inhibitor of miR-379 or a portion or fragment thereof and of miR-541 or a portion or fragment thereof, and/or of the respective target sites of said miRs, thus preventing the miRs from docking to the target site to silence the respective mRNA. As readily understood by the skilled person, such inhibitor of a target site of miR-379 or a portion or fragment thereof or of miR-541 or a portion or fragment thereof does not interfere with proper translation of the respective mRNA and does not cleave or destabilize said mRNA, or at least to a lower extent compared to the respective miR-379 or a portion or fragment thereof or miR-541 or a portion or fragment thereof itself.

Furthermore, as used herein, the term "microRNA", "miRNA" or "miR" are used interchangeably and typically comprise non-coding RNA between 18 and 26 nucleobases in length, which may be the product of cleavage of a pre-miRNA by the enzyme Dicer. Examples of mature miRNAs are found in a miRNA database known in the art such as miRBase (miRbase.org).

Furthermore, as used herein, the term "inhibiting" or "inhibitor of" miR-379 or miR-541 (or of the respective target site) or a portion or fragment thereof, respectively, comprises that the binding or docking between miR-379 or a portion or fragment thereof or miR-541 or a portion or fragment thereof to its respective target site is inhibited or suppressed, e.g., either by directly binding the respective miR or its target site, or by supporting or inducing cleavage or degradation of miR-379 or miR-541, or otherwise impairing the function and/or expression of miR-379 or a portion or fragment thereof or of miR-541 or a portion or fragment thereof, respectively. For example, the inhibitor may be or comprise a nucleic acid molecule. In one aspect of the present invention, the inhibitor of miR-379 or a portion or fragment thereof and/or of miR-541 or a portion or fragment thereof may serve as an antisense molecule to the respective miR.

In context of the present invention, the inhibitor of miR-379 or a portion or fragment thereof and the inhibitor of miR-541 or a portion or fragment thereof as comprised by the composition described and provided herein may be in the same molecule or on different molecules. For example, the composition of the present invention may comprise a nucleic acid molecule comprising both, a sequence serving as inhibitor of miR-379 or a portion or fragment thereof, and a sequence serving as inhibitor of miR-541 or a portion or fragment thereof, or it may comprise two different nucleic acid molecules, one comprising a sequence serving as inhibitor of miR-379 or a portion or fragment thereof, and the other one comprising a sequence serving as inhibitor of miR-541 or a portion or fragment thereof. In one embodiment of the present invention, the composition comprises an inhibitor of miR-379 or a portion or fragment thereof and an inhibitor of miR-541 or a portion or fragment thereof on the same molecule, wherein said molecule comprises both, a nucleotide sequence complementary to or hybridizing as described herein (e.g., under stringent conditions) to miR-379 or a portion or fragment thereof and a nucleotide sequence complementary to or hybridizing as described herein (e.g., under stringent conditions) to miR-541 or a portion or fragment thereof.

Generally, as used herein, the terms "polynucleotide", "nucleic acid" or "nucleic acid molecule" are to be construed synonymously. Generally, nucleic acid molecules may comprise inter alia DNA molecules, RNA molecules, oligonucleotide thiophosphates, substituted ribo-oligonucleotides or PNA molecules. Furthermore, the term "nucleic acid molecule" may refer to DNA or RNA or hybrids thereof or any modification thereof that is known in the art (see, e.g., U.S. Pat. Nos. 5,525,711, 471,1955, 5,792,608 or EP 302175 for examples of modifications). The polynucleotide sequence may be single- or double-stranded, linear or circular, natural or synthetic, and without any size limitation. For instance, the polynucleotide sequence may be genomic DNA, cDNA, mitochondrial DNA, RNA, antisense RNA, ribozymal RNA or a DNA encoding such RNAs or chimeroplasts (Gamper, Nucleic Acids Research, 2000, 28, 4332-4339). Said polynucleotide sequence may be in the form of a vector, plasmid or of viral DNA or RNA. Also described herein are nucleic acid molecules, which are complementary to the nucleic acid molecules described above and nucleic acid molecules, which are able to hybridize to nucleic acid molecules described herein. A nucleic acid molecule described herein may also be a fragment of the nucleic acid molecules in context of the present invention. Particularly, such a fragment is a functional fragment. Examples for such functional fragments are nucleic acid molecules, which can serve as primers.

As used herein, nucleic acid molecules may comprise different types of nucleotides, comprising naturally occurring nucleotides, modified nucleotides, and artificial nucleotides. Nucleotides as used herein generally comprise nucleosides, naturally occurring nucleosides, modified nucleosides, and artificial nucleosides. As known in the art, naturally occurring nucleosides comprise purin bases or pyrimidin bases. Examples for naturally occurring nucleosides comprise (deoxy)adenosine, (deoxy)guanosine, (deoxy)uridine, thymidine, and (deoxy)cytidine. Nucleosides as part of nucleotides (and, thus, nucleic acid molecules) as described herein may generally encompass structures comprising any purine or pyrimidine nucleoside and derivatives or analogues thereof. That is, "purine nucleoside" or "pyrimidine nucleoside" as used in context with the present invention generally comprises any kind of purine or pyrimidine as well as derivatives or analogues thereof as described herein respectively, as well as a sugar, e.g., a pentose. In one embodiment of the present invention, the purine nucleoside may be selected from the group consisting of (deoxy) adenosine, inosine, and (deoxy)guanosine and derivatives or analogues thereof. A derivative may be, e.g., a nucleoside with a purine selected from the group consisting of a deazapurine, an azidopurine, an alkylpurine, a thiopurine, a bromopurine, an O-alkylpurine, and an isopurine, for example, a deazapurine such as, e.g., 7-deazapurine. That is, in one aspect of the present invention, the purine nucleoside may be a nucleoside with a purine selected from the group consisting of a deazapurine, an azidopurine, an alkylpurine, a thiopurine, a bromopurine, an O-alkylpurine, and an isopurine, for example a deazapurine such as, e.g., 7-deazapurine. In another aspect of the present invention, the purine nucleoside may be selected from the group consisting of 1-methyl-(deoxy)adenosine, 2-methyl-(deoxy) adenosine, $N^6$-methyl-(deoxy)adenosine, $N^6,N^6$-dimethyl-(deoxy)adenosine, 7-deaza-(deoxy) adenosine, 7-deaza-8-aza(deoxy)adenosine, 7-deaza-7-bromo(deoxy)adenosine, 7-deaza-7-iodo(deoxy)adenosine, 8-azido(deoxy)adenosine, 8-bromo(deoxy)adenosine, 8-iodo(deoxy)adenosine, 8-bromo-2'-deoxy(deoxy)adenosine, 2'-O-methyladenosin, inosin, 1-methylinosin, 2'-O-methylinosin, 1-methyl(deoxy) guanosine, 7-methyl(deoxy)guanosine, $N^2$-methyl(deoxy) guanosine, $N^2,N^2$-dimethyl-guanosine, isoguanosine, 7-deaza(deoxy)guanosine, 7-deaza-8-aza(deoxy)guanosine, 7-deaza-7-bromo(deoxy)guanosine, 7-deaza-7-iodo(deoxy) guanosine, 6-thio(deoxy)guanosine, $O^6$-methyl(deoxy) guanosine, 8-azido(deoxy)guanosine, 8-bromo(deoxy) guanosine, 8-iodo(deoxy)guanosine, 2'-O-methylguanosine, 8-azidoinosine, 7-azainosine, 8-bromoinosine, 8-iodoinosine, 1-methylinosine, and 4-methylinosine. In a further aspect of the present invention, the purine nucleosides may be selected from the group consisting of a queuosine, an archaeosine, a wyosine and a $N^6$-threonylcarbamoyladenosine. In one aspect of the present invention, the pyrimidine nucleoside may be selected from the group consisting of (deoxy)cytidine, (deoxy)thymidine, (deoxy)ribothymidine, (deoxy)uridine, and derivatives thereof. A derivative may be, e.g., a nucleoside with a pyrimidine selected from the group consisting of an alkylpyrimidine, a thiopyrimidine, a bromopyrimidine, an O-alkylpyrimidine, an isopyrimidine, an acetylpyrimidine hydropyrimidine, and a pseudopyrimidine. That is, in one aspect of the present invention, the pyrimidine nucleoside may be a nucleoside with a pyrimidine selected from the group consisting of an alkylpyrimidine, a thiopyrimidine, a bromopyrimidine, an O-alkylpyrimidine, an isopyrimidine, an acetylpyrimidine hydropyrimidine, and a pseudopyrimidine. In another aspect of the present invention, the pyrimidine nucleoside may be selected from the group consisting of 3-methyl-(deoxy) cytidine, $N^4$-methyl(deoxy)cytidine, $N^4,N^4$-dimethyl(deoxy)cytidine, iso(deoxy)cytidine, pseudo(deoxy)cytidine, pseudoiso(deoxy)cytidine, 2-thio(deoxy)cytidine, $N^4$-acetyl (deoxy)cytidine, 3-methyl(deoxy)uridine, pseudo(deoxy)uridine, 1-methyl-pseudo (deoxy)uridine, 5,6-dihydro(deoxy) uridine, 2-thio(deoxy)uridine, 4-thio(deoxy)uridine, 5-bromodeoxy(deoxy)uridine, 2'-deoxyuridine, 4-thio(deoxy) thymidine, 5,6-dihydro(deoxy)thymidine, $O^4$-methylthymidine, difluortoluene, and other nucleobase surrogates. As mentioned, the nucleosides as described and provided herein generally comprise a purine or pyrimidine or derivative or analogue thereof as described herein as well as sugar moiety such as, e.g., a pentose. Generally, the pentose as part of the purine or pyrimidine nucleoside or derivative or analogue thereof as described herein may be, inter alia, ribose, deoxyribose, arabinose, or methylribose (2-O-methyribose), for example, a ribose or a deoxyribose. That is, the nucleoside may be, e.g., a (ribosyl) nucleoside, a desoxy (ribosyl) nucleoside, an arabinosylnucleoside or an (methylribosyl) nucleoside, for example a (ribosyl) nucleoside or a deoxy (ribosyl) nucleoside.

As used herein, the terms "desoxy" and "deoxy" as prefixes of molecule terms are used synonymously and indicate the absence of an oxygen atom or a hydroxyl-group, e.g., in a given pentose such as ribose or others.

In one aspect of the present invention, the inhibitor of miR-379 and/or miR-541 or a portion or fragment thereof, respectively, may serve as an antisense molecule to the respective miR. In one embodiment of the present invention, at least one (or all) inhibitor(s) of miR-379 or a portion or fragment thereof comprise(s) a nucleotide sequence complementary to or hybridizing (e.g., under stringent conditions) to miR-379 or a portion or fragment thereof, and at least one (or all) inhibitor(s) of miR-541 or a portion or fragment thereof comprises a nucleotide sequence complementary to or hybridizing (e.g., under stringent conditions) to miR-541 or a portion or fragment thereof. In this context, it is possible that the inhibitor of miR-379 or a portion or fragment thereof and the inhibitor of miR-541 or a portion or fragment thereof are located on different molecules, or they may be located on a single molecule, i.e. one molecule comprises both, an inhibitor of miR-379 or a portion or fragment thereof and an inhibitor of miR-541 or a portion or fragment thereof. In one embodiment of the present invention, the inhibitor of miR-379 or a portion or fragment thereof and the inhibitor of miR-541 or a portion or fragment thereof are located on a single molecule.

The term "hybridization" or "hybridizes" as used herein in context with inhibitors and nucleic acid molecules/DNA sequences incl. miRs or a portion or fragment thereof may relate to hybridizations under stringent, low stringent or non-stringent conditions. In one embodiment, the conditions are preferably stringent. Said hybridization conditions may be established according to conventional protocols described, for example, in Sambrook, Russell "Molecular Cloning, A Laboratory Manual", Cold Spring Harbor Laboratory, N. Y. (2001); Current Protocols in Molecular Biology, Update May 9, 2012, Print ISSN: 1934-3639, Online ISSN: 1934-3647; Ausubel, "Current Protocols in Molecular Biology", Green Publishing Associates and Wiley Interscience, N. Y. (1989), or Higgins and Hames (Eds.), "Nucleic acid hybridization, a practical approach", IRL Press Oxford, Washington DC, (1985). The setting of conditions is well within the skill of the artisan and can be determined according to protocols described in the art. Thus, the detection of only specifically hybridizing sequences will usually require stringent hybridization and washing conditions such as 0.1×SSC, 0.1% SDS at 65° C. ("stringent conditions" as used herein). Non-stringent hybridization conditions for the detection of homologous or not exactly complementary sequences may be set at 6×SSC, 1% SDS at 65° C. ("non-stringent conditions" as used herein). As is well known, the length of the probe and the composition of the nucleic acid to be determined constitute further parameters of the hybridization conditions. Variations in the above conditions may be accomplished through the inclusion and/ or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. In accordance to the invention described herein, low stringent hybridization conditions for the detection of homologous or not exactly complementary sequences may, for example, be set at 6×SSC, 0.5% SDS at 65° C. ("low stringent conditions" as used herein). As is well known, the length of the probe and the composition of the nucleic acid to be determined constitute further parameters of the hybridization conditions.

Hybridizing nucleic acid molecules also comprise fragments of the above described molecules. Such fragments may represent nucleic acid molecules serving as inhibitors as described herein or a functional fragment thereof. Furthermore, nucleic acid molecules, which hybridize with any of the aforementioned nucleic acid molecules, also include complementary fragments, derivatives and variants of these molecules. Additionally, a hybridization complex refers to a complex between two nucleic acid sequences by virtue of the formation of hydrogen bonds between complementary G and C bases and between complementary A and T (or U for RNA as known to the skilled person) bases; these hydrogen bonds may be further stabilized by base stacking interactions. The hydrogen bonds may be in an antiparallel configuration. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed). The terms "complementary" or "complementarity" refer to the natural binding of polynucleotides under permissive salt and temperature conditions by base-pairing. For example, the sequence "A-G-U" binds to the complementary sequence "U-C-A". Complementarity between two single-stranded molecules may be "partial", in which only some of the nucleic acids bind, or it may be complete when total complementarity exists between single-stranded molecules. The degree of complementarity between nucleic acid strands has significant effects on the efficiency and strength of hybridization between nucleic acid strands. This is of particular importance in amplification reactions, which depend upon binding between nucleic acids strands. The term "hybridizing sequences" preferably refers to sequences, which display a sequence identity of at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 95%, more preferably at least 96%, more preferably at least 97%, more preferably at least 98%, more preferably at least 99%, more preferably at least 99.5%, and most preferably 100% identity with a nucleic acid sequence as described herein serving as an inhibitor as described and provided herein.

As used herein, a "portion" or "fragment" of a given microRNA (miRNA) may be any portion of a microRNA and may particularly comprise portions of a microRNA or precursor thereof (e.g., pri- or pre-microRNA) comprising or consisting of at least 10, 11, 12, 13, 14, 15, 16, 17, 18, 19, 20, 21 or 22 consecutive nucleotides of the respective microRNA or precursor thereof. In one embodiment, a portion or fragment of a given microRNA is a portion or fragment, which prevails in the cell after (nuclear and/or cytoplasmic) processing of the microRNA (e.g., pri- or pre-microRNAs), e.g., the 5p-arm (also referred to as 5p-strand) or 3p-arm (also referred to as 3p-strand) of the respective miR. In one embodiment of the present invention, a portion or fragment of a microRNA is the 5p-arm of a microRNA or its precursor. For example, in accordance with the present invention, a portion or fragment of miR-379 may be inter alia miR-379-5p, and/or a portion or fragment of miR-541 may be inter alia miR-541-5p. In one embodiment of the present invention, a portion or fragment of a microRNA is the 3p-arm of a microRNA or its precursor. For example, in accordance with the present invention, a portion or fragment of miR-379 may be inter alia miR-379-3p, and/or a portion or fragment of miR-541 may be inter alia miR-541-3p.

In this context, as it is readily understood by the person skilled in the art, and in accordance with the present invention, an inhibitor of a portion or fragment of a given microRNA is also an inhibitor of the microRNA itself or its precursors, as inhibiting the portion or fragment as defined herein also inhibits the whole microRNA from its function as defined herein.

Accordingly, as used herein, an inhibitor of a microRNA (e.g., miR-379 or miR-541) or its precursor may also comprise an inhibitor of a portion or fragment of that microRNA (e.g., miR-379 or miR-541), respectively if that inhibitor binds or is complementary to or hybridizes (e.g., under stringent conditions) to that portion or fragment. Likewise, in accordance with the present invention, an inhibitor of a portion or fragment of that microRNA (e.g., miR-379 or miR-541) also comprises an inhibitor of that respective microRNA (e.g., miR-379 or miR-541) or its precursor.

In one embodiment of the present invention, a portion or fragment of miR-379 is miR-379-5p and has a nucleotide sequence according to SEQ ID NO: 1, wherein not more than 6, 5, 4, 3, 2 or 1 nucleotides are substituted. For example, the nucleotides, which are substituted compared to SEQ ID NO: 1 may be any other nucleotide, which allows hybridization of the respective inhibitor as described herein. In one embodiment of this invention, said substitutions may be located within the last 6, 5, 4, 3, 2 or 1 nucleotides of the 3'-end of SEQ ID NO: 1 and/or at the first nucleotide of the 5'-end of SEQ ID NO: 1. In a specific embodiment of the present invention, a portion or fragment of miR-379 is miR-379-5p and has a nucleotide sequence according to SEQ ID NO: 1.

In a further embodiment of the present invention, a portion or fragment of miR-541 is miR-541-5p and has a nucleotide sequence according to SEQ ID NO: 2, wherein not more than 8, 7, 6, 5, 4, 3, 2 or 1 nucleotides are substituted. For example, the nucleotides, which are substituted compared to SEQ ID NO: 2 may be any other nucleotide, which allows hybridization of the respective inhibitor as described herein. In one embodiment of this invention, said substitutions may be located within the last 8, 7, 6, 5, 4, 3, 2 or 1 nucleotides of the 3'-end of SEQ ID NO: 2 and/or at the first nucleotide of the 5'-end of SEQ ID NO: 2. In a specific embodiment of the present invention, a portion or fragment of miR-541 is miR-541-5p and has a nucleotide sequence according to SEQ ID NO: 2.

In one embodiment of the composition of the present invention, a portion of miR-379 has a nucleotide sequence according to SEQ ID NO: 1, wherein not more than 6 nucleotides are substituted, and a portion of miR-541 has a nucleotide sequence according to SEQ ID NO: 2, wherein not more than 8 nucleotides are substituted.

The inhibitor comprised by the composition described and provided by the present invention may be any inhibitor, which is preferably capable of inhibiting or suppressing the binding or docking between miR-379 (or a portion or fragment thereof) or miR-541 (or a portion or fragment thereof) to its respective target site, e.g., either by directly binding the respective miR or its target site, or by supporting or inducing cleavage or degradation of miR-379 (or a portion or fragment thereof) or miR-541 (or a portion or fragment thereof), or otherwise impairing the function and/or expression of miR-379 (or a portion or fragment thereof) or miR-541 (or a portion or fragment thereof), respectively. For example, the inhibitor may be or comprise a nucleic acid molecule.

In one embodiment of the present invention, at least one inhibitor comprises a nucleic acid sequence comprising at least 10, 11, 12, 13, 14, 15, 16, 17, 18, 19 or 20 nucleotides, for example at least 15 or 16 nucleotides. In a further embodiment of the present invention, the inhibitor does not exceed the length of 250, 200, 150, 140, 130, 120, 110, 100, 90, 80, 70, 60, 50, 45, 40, 35, 30, or 25 nucleotides.

In context with the present invention, the inhibitor of miR-379 (or a portion or fragment thereof) and/or miR-541 (or a portion or fragment thereof) may directly target the respective miR or portions thereof or fragments thereof as described herein. General inhibitory molecules capable of inhibiting a miR are known in the art. In one embodiment of the present invention, the inhibitor to miR-379 (or a portion or fragment thereof) and/or miR-541 (or a portion or fragment thereof) may be selected from the group consisting of Tough Decoys (TuD) (e.g., Tough Decoy RNA), Decoys, antisense oligonucleotides (antisense RNA or DNA, chimeric antisense molecules), anti-miR, block-miR, ribozymes, external guide sequence (EGS), oligonucleotides, small interference RNA (siRNA), small temporal RNA (stRNA), short hairpin RNA (shRNA), small RNA-induced gene activation (RNAa), small activating RNA (saRNA), locked nucleic acids (LNA), antagomirs, and peptide nucleic acids (PNA) and other oligomeric nucleic acid molecules, which are able to inhibit or suppress the function of the respective miR as described herein (e.g., by hybridizing to at least a portion of the target site of the respective miR). In a specific embodiment of the present invention, the at least one inhibitor is a Tough Decoy RNA (TuD). Tough decoys are generally known in the art and available, e.g., from Signa-Gen® Laboratories (USA). In context with the present invention, the composition of the present invention may, e.g., comprise a TuD comprising both, a sequence inhibiting miR-379 (or a portion or fragment thereof) and another sequence inhibiting miR-541 (or a portion or fragment thereof) on the same TuD-molecule, or the composition of the present invention may comprise two different TuDs, one comprising a sequence inhibiting miR-379 (or a portion or fragment thereof) and the other one comprising a sequence inhibiting miR-541 (or a portion or fragment thereof). For example, the composition of the present invention comprises a TuD comprising both, a sequence inhibiting miR-379 (or a portion or fragment thereof) and another sequence inhibiting miR-541 (or a portion or fragment thereof) on the same TuD-molecule. In a specific embodiment of the present invention, said inhibitor comprises the nucleotide sequence of SEQ ID NO: 5, wherein not more than 10, 9, 8, 7, 6, 5, 4, 3, 2, or 1 nucleotides are substituted compared to SEQ ID NO: 5. In a further specific embodiment of the present invention, said inhibitor is a nucleic acid molecule comprising the nucleotide sequence of SEQ ID NO: 5.

Furthermore, the inhibitor comprised by the composition described and provided herein may also comprise a chemical modification, e.g., in order to improve stability or allow proper administration to a subject in need thereof. In one embodiment of the present invention, at least one inhibitor comprises a chemical modification of the nucleic acid sequence selected from the group consisting of nucleic acid analogs comprising N-acetylgalactosamine (GalNAc), phosphorothioate DNA (PS), 2'-O-methyl RNA (OMe), 2'-O-methoxy-ethyl RNA (MOE), peptide nucleic acid (PNA), N3'-P5'-phosphoroamidate (NP), 2'-fluoro-arabino nucleic acid (FANA), morpholino phosphoroamidate (MF), cyclo-hexene nucleic acid (CeNA), and tricycleDNA (tc-DNA).

In another embodiment of the present invention, the inhibitor may also be comprised by a suitable vehicle or carrier. Thus, the present invention also relates to vehicles and carriers comprising the composition comprising the inhibitors as described and provided herein. For example, in context with the present invention, at least one inhibitor may be comprised by a delivery vehicle selected from the group consisting of adeno-associated virus (AAV), lentiviral vector, polyethylene imine (PEI), cationic liposomes (e.g. lipid nanoparticles), silica nanoparticles, PEGylated PLGA, and neutral lipid. The vehicle of the present invention may serve the purpose for assuring the uptake of the composition of the present invention at the intended target site in a subject that requires treatment with such a composition. In context with the present invention, further exemplary delivery vehicles for an inhibitor described herein include lipid (e.g., cationic lipid) containing vehicles (e.g., liposomes), viral containing vehicles (e.g., vectors), polymer containing vehicles (e.g., biodegradable polymers or dendrimers), and peptide containing vehicles (e.g., a penetration peptide), exosomes, and bacterially-derived, intact minicells. In a specific embodiment of the present invention, the delivery vehicle includes more than one compound. For example, it may include one or more lipid moieties, one or more peptides, one or more polymers, one or more viral vectors, or a combination thereof. Specific embodiments pertain to a delivery vehicle, which is an association complex, such as a liposome. A liposome generally includes a plurality of components, such as one or more of a cationic lipid (e.g., an amino lipid), a targeting moiety, a fusogenic lipid, a PEGylated lipid. In some embodiments, the PEG-lipid may be a targeted PEG-lipid. For example, a liposome can include a nucleic acid and an amine-lipid and a PEGylated lipid. In some embodiments of the present invention, the PEG-lipid is a targeted PEG-lipid. In further embodiments, the preparation also includes a structural moiety such as cholesterol. Most preferred in context of the present invention is a viral delivery vehicle. The viral vector may be, e.g., a retrovirus, such as a lentivirus, or an adenovirus, preferably an adeno-associated virus (e.g., AAV). Thus, the present invention also provides a viral vector, comprising an inhibitor of miR-379 (or a portion or fragment thereof) and miR-541 (or a portion or fragment thereof) as described herein, and/or a composition comprising a viral vector comprising an inhibitor of miR-379 (or a portion or fragment thereof) as described herein and a viral vector comprising an inhibitor of miR-541 (or a portion or fragment thereof) as described herein. Where the inhibitors are nucleic acid molecules, their sequences may be, e.g., inserted into an untranslated region of a gene, the gene being part of a construct or cassette, which is then delivered by the vector. When transduced, a host cell may express the sequence of the present invention and therefore silence or express any miR of the present invention. The vector may be the viral capsid and may not comprise any viral or other polynucleotides, other than the present construct.

As already mentioned, the inhibitor of the composition described and provided herein may be a nucleic acid molecule. For example, at least one (or all) inhibitor(s) of miR-379 (or a portion or fragment thereof) comprise(s) a nucleotide sequence complementary to or hybridizing (e.g., under stringent conditions) to miR-379 (or a portion or fragment thereof), and at least one (or all) inhibitor(s) of miR-541 (or a portion or fragment thereof) comprise(s) a nucleotide sequence complementary to or hybridizing (e.g., under stringent conditions) to miR-541 (or a portion or fragment thereof). In one embodiment of the present invention, the inhibitor of miR-379 comprises a nucleotide sequence of SEQ ID NO: 3, wherein not more than 5, 4, 3, 2, or 1 nucleotide(s) is/are substituted. Also, in a further embodiment, not more than 30, 25, 20, 15, 10, 6 or 5 nucleotides are added compared to SEQ ID NO: 3. For example, the nucleotides, which are added or substituted compared to SEQ ID NO: 3 may be any other nucleotide, which allows hybridization of the inhibitor to miR-379 as described herein. In one embodiment, where nucleotides are added to SEQ ID NO: 3, such added nucleotides are added in such a manner to further increase hybridization to a nucleic acid sequence according to SEQ ID NO: 1. For example, up to 5, 4, 3, 2, or 1 nucleotide(s) is/are added to the 5'-end of SEQ ID NO: 3, e.g., 5'-CCUTC-3' or any subset of nucleotides thereof. In a specific embodiment of the present invention, the inhibitor of miR-379 is a nucleic acid molecule having the sequence of SEQ ID NO: 3.

In a further embodiment of the present invention, the inhibitor of miR-541 comprises a nucleotide sequence of SEQ ID NO: 4, wherein not more than 5, 4, 3, 2, or 1 nucleotide(s) is/are substituted. Also, in a further embodiment, not more than 30, 25, 20, 15, 10, 9 or 8 nucleotides are added compared to SEQ ID NO: 4. For example, the nucleotides, which are added or substituted compared to SEQ ID NO: 4 may be any other nucleotide, which allows hybridization of the inhibitor to miR-541 as described herein. In one embodiment, where nucleotides are added to SEQ ID NO: 4, such added nucleotides are added in such a manner to further increase hybridization to a nucleic acid sequence according to SEQ ID NO: 2. For example, up to 8, 7, 6, 5, 4, 3, 2, or 1 nucleotide(s) is/are added to the 5'-end of SEQ ID NO: 4, e.g., 5'-TGUGUGTC-3' or any subset of nucleotides thereof. In a specific embodiment of the present invention, the inhibitor of miR-541 is a nucleic acid molecule having the sequence of SEQ ID NO: 4.

In a further embodiment of the composition of the present invention, the inhibitor of miR-379 or a portion or fragment thereof comprises a nucleotide sequence of SEQ ID NO: 3, wherein not more than 5 nucleotides are substituted, and/or the inhibitor of miR-541 or a portion or fragment thereof comprises a nucleotide sequence of SEQ ID NO: 4, wherein not more than 5 nucleotides are substituted.

The present invention also relates to pharmaceutical compositions comprising a composition and/or a vehicle or carrier comprising such composition as described and provided herein.

The present invention also relates to a composition, a vehicle or carrier, and/or a pharmaceutical composition as described and provided herein, for use in treating or preventing a metabolic dysfunction, disease or disorder related to lipid (e.g., triglyceride) and sugar (e.g., glucose) metabolism, and/or related to cancer. In one embodiment of the present invention, such metabolic dysfunction, disease or disorder may comprise glucocorticoid hormone driven metabolic dysfunction, obesity, diabetes (type 1 and 2), diabesity, metabolic syndrome, insulin resistance, hyperglycemia, (systemic) dyslipidemia, Cushing's syndrome, adverse or side effects associated with or caused by glucocorticoid (GC) treatment or excess, atherosclerosis, heart disease, stroke, (cancer) cachexia, growth defects, hepatic steatosis, NASH, and liver fibrosis. In context with the present invention, the composition, vehicle or carrier, and/or pharmaceutical composition as described and provided herein may also be for use in (personal) diabetes type 1 and/or 2 therapy. In a further embodiment of the present invention, such cancer to be treated as described herein may comprise hepatocellular carcinoma HCC and tumors that have been shown to be correlated with metabolic dysfunction, e.g. obesity, including pancreatic cancer, colon cancer, endometrial cancer, breast cancer, esophageal cancer, and gastric cancer.

The embodiments, which characterize the present invention, are described herein, shown in the Figures, illustrated in the Examples, and reflected in the claims.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or", wherever used herein, includes the meaning of "and", "or" and "all or any other combination of the elements connected by said term".

The term "about" or "approximately" as used herein means within 20%, preferably within 10%, more preferably within 5%, and most preferably within 3% of a given value or range.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

Unless specifically stated otherwise, in each instance herein any of the terms "comprising", "consisting essentially of" and "consisting of" may be replaced with either of the other two terms. For example, where a given feature, compound or range is indicted as "comprised by" a respective broader term, such broader term may also "consist of" such feature, compound or range.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent, the material incorporated by reference contradicts or is inconsistent with this specification, the specification will supersede any such material.

The Figures show:

FIG. 1: Experimental protocol for the liver-specific inhibition of miR-541 and miR-379 activity by rAAV-mediated delivery of TuD inhibitors in mice.

Figure 2:
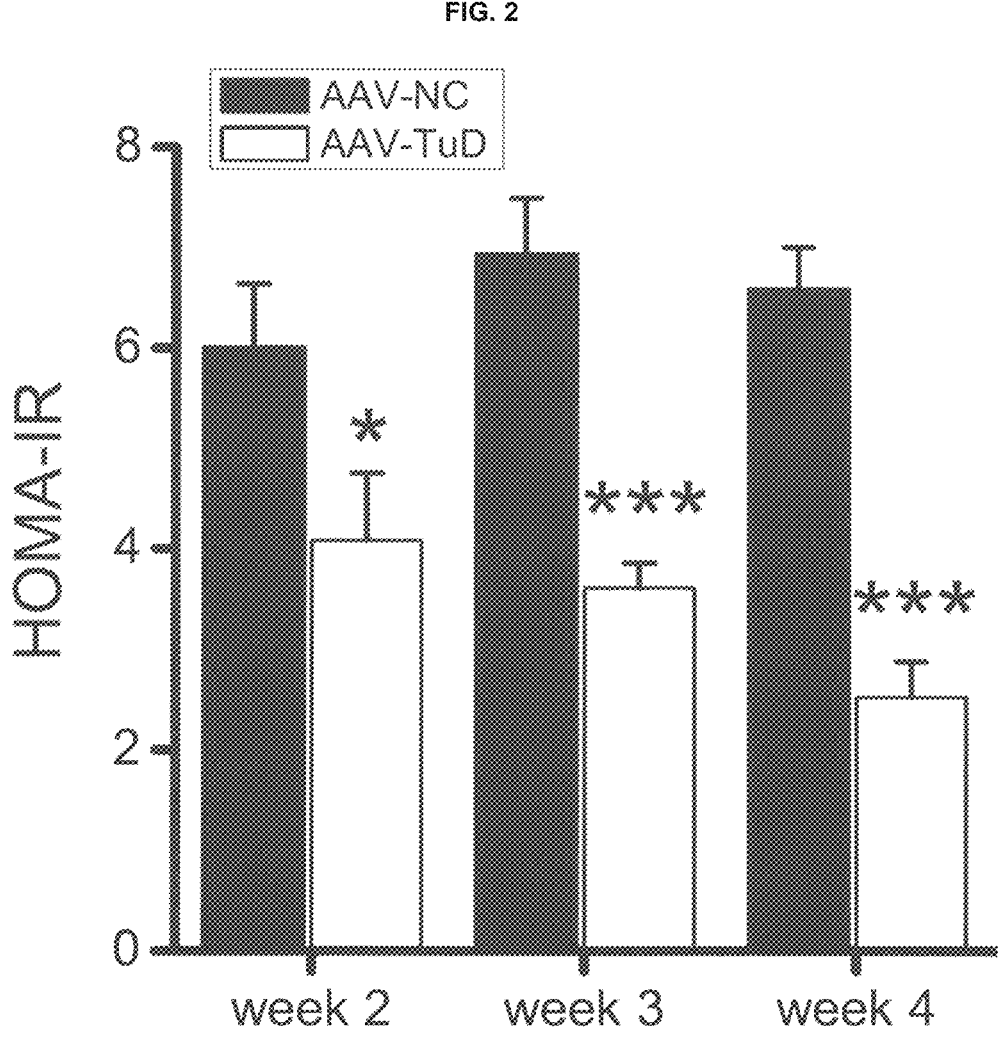

FIG. 2: Reduction in HOMA-IR (surrogate measurement of insulin resistance) observed in animals with hepatic-specific inhibition of miR-541 and miR-379 activity (AAV-TuD, white bar) as compared to negative control (AAV-NC, black bar).

Figure 3:
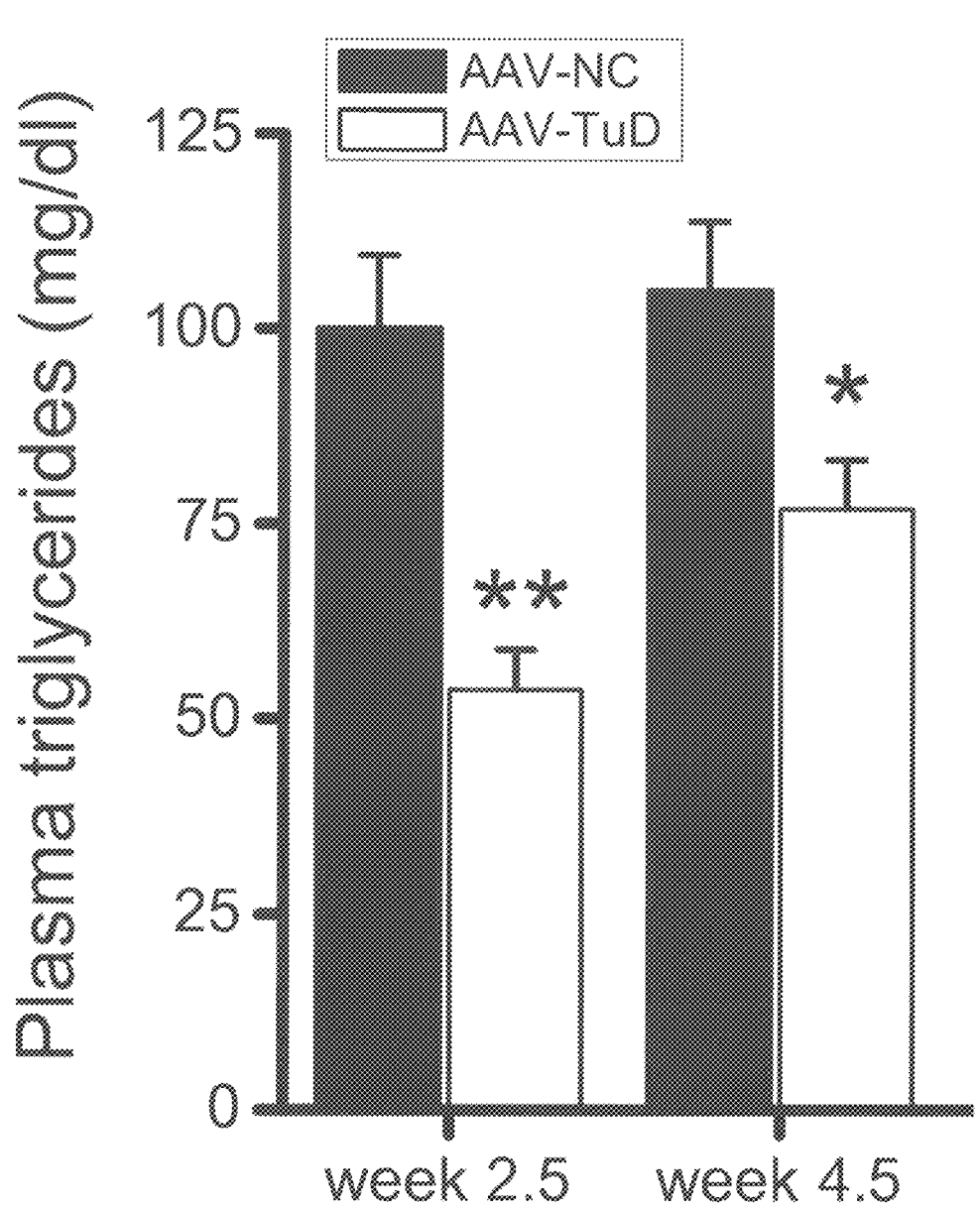

FIG. 3: Decreased circulating levels of triglycerides in animals with hepatic-specific inhibition of miR-541 and miR-379 activity (AAV-TuD, white bar) as compared to negative control (AAV-NC, black bar).

Figure 4:
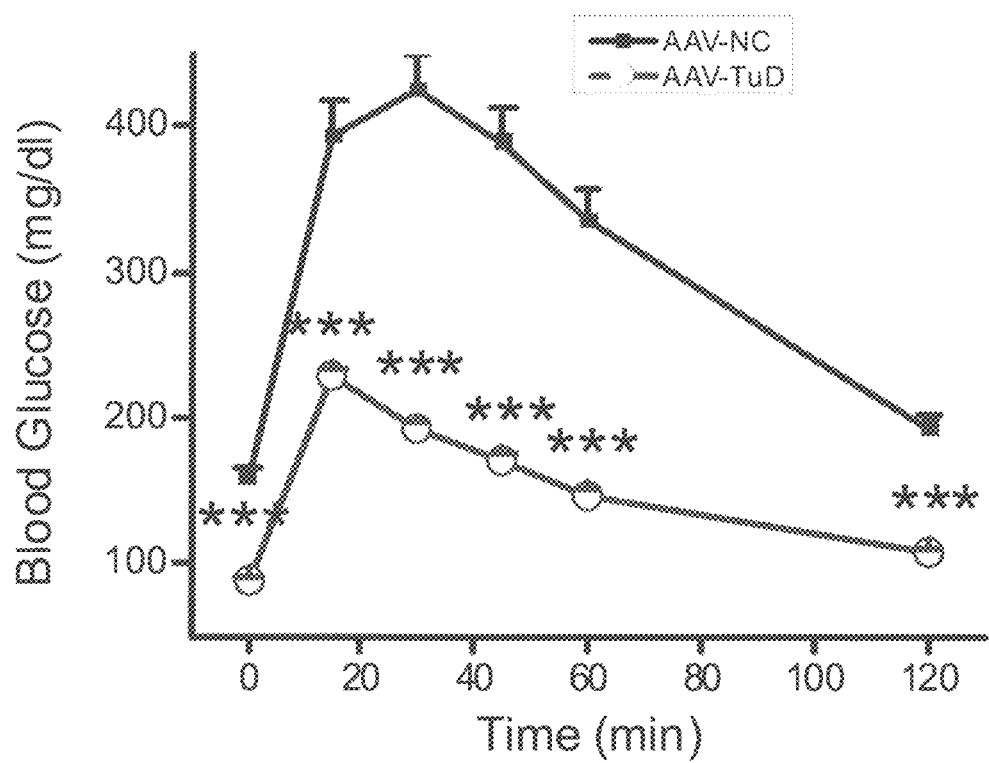
Figure 4:
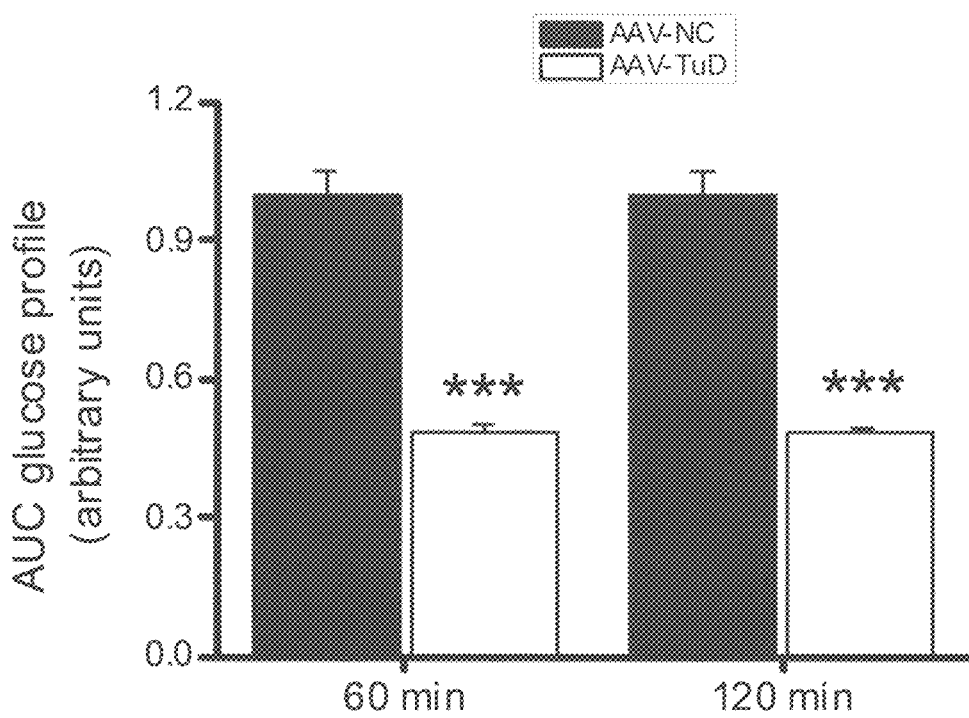

FIG. 4: Improvement in glucose clearance following an intraperitoneal glucose load (2 g/kg) in mice with hepatic-specific inhibition of miR-541 and miR-379 activity (AAV- TuD, open circles and white bar) as compared to negative control (AAV-NC, closed squares and black bar). Glucose profile (A) and area under the curve (B).

Figure 5:
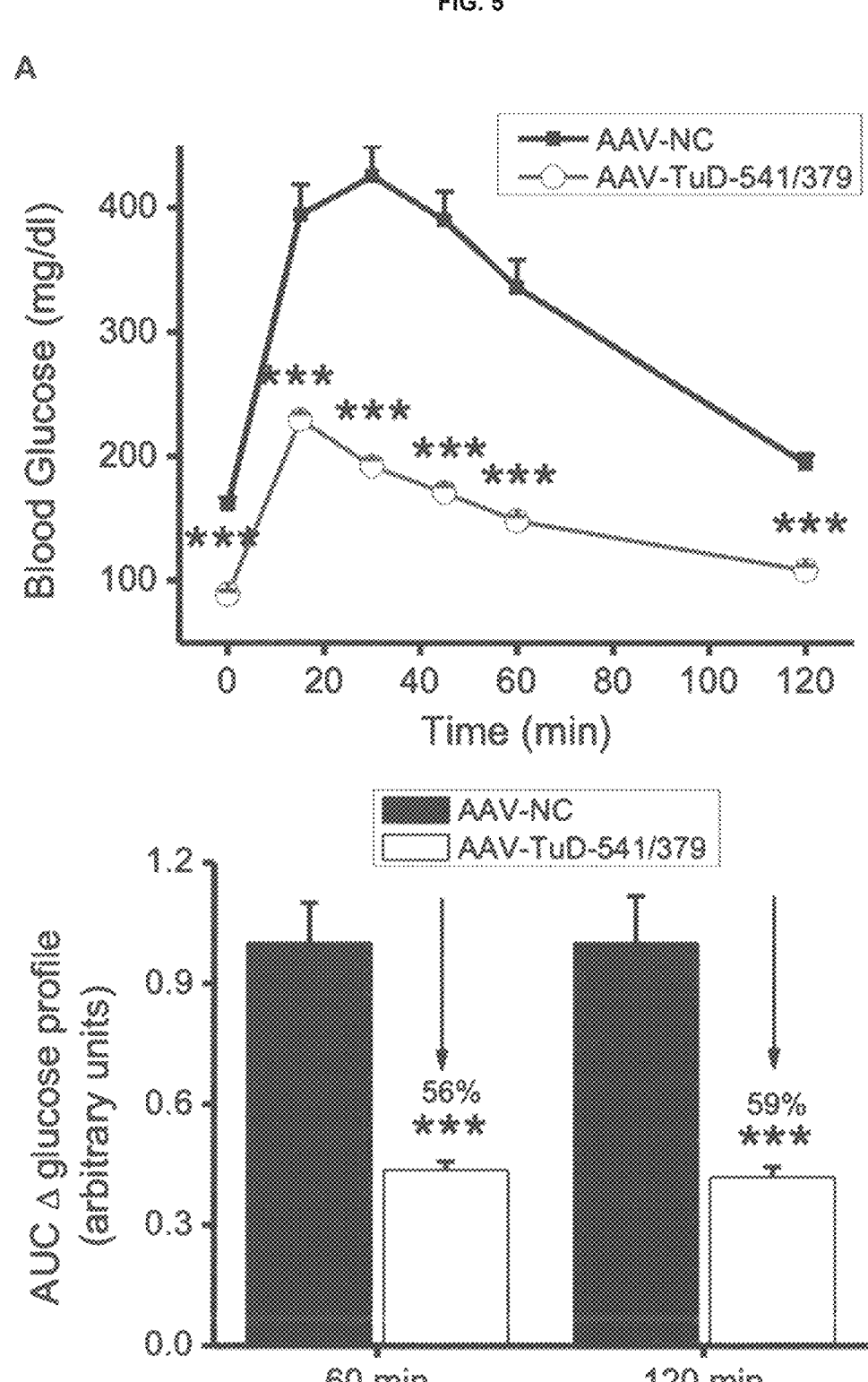
Figure 5:
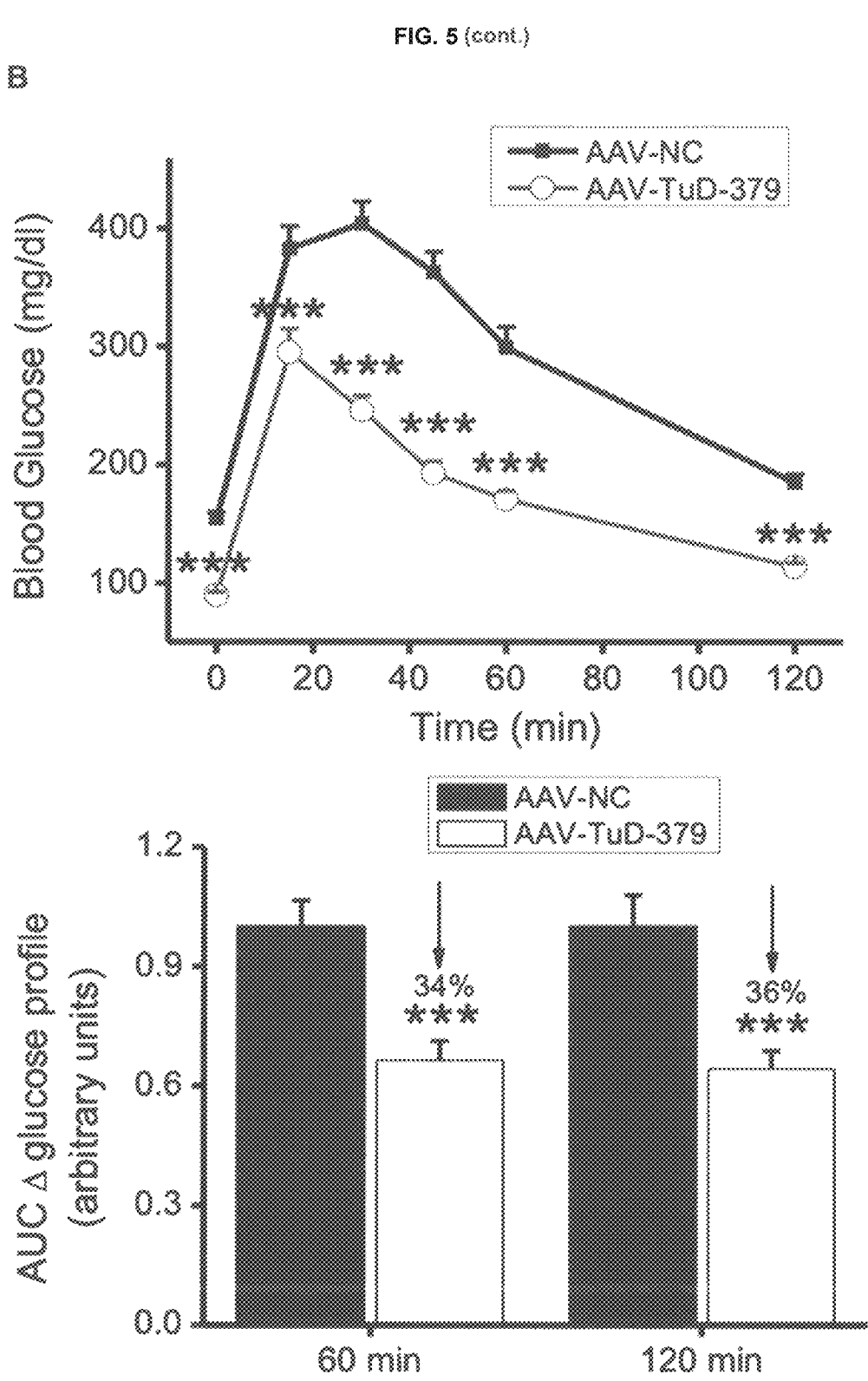
Figure 5:
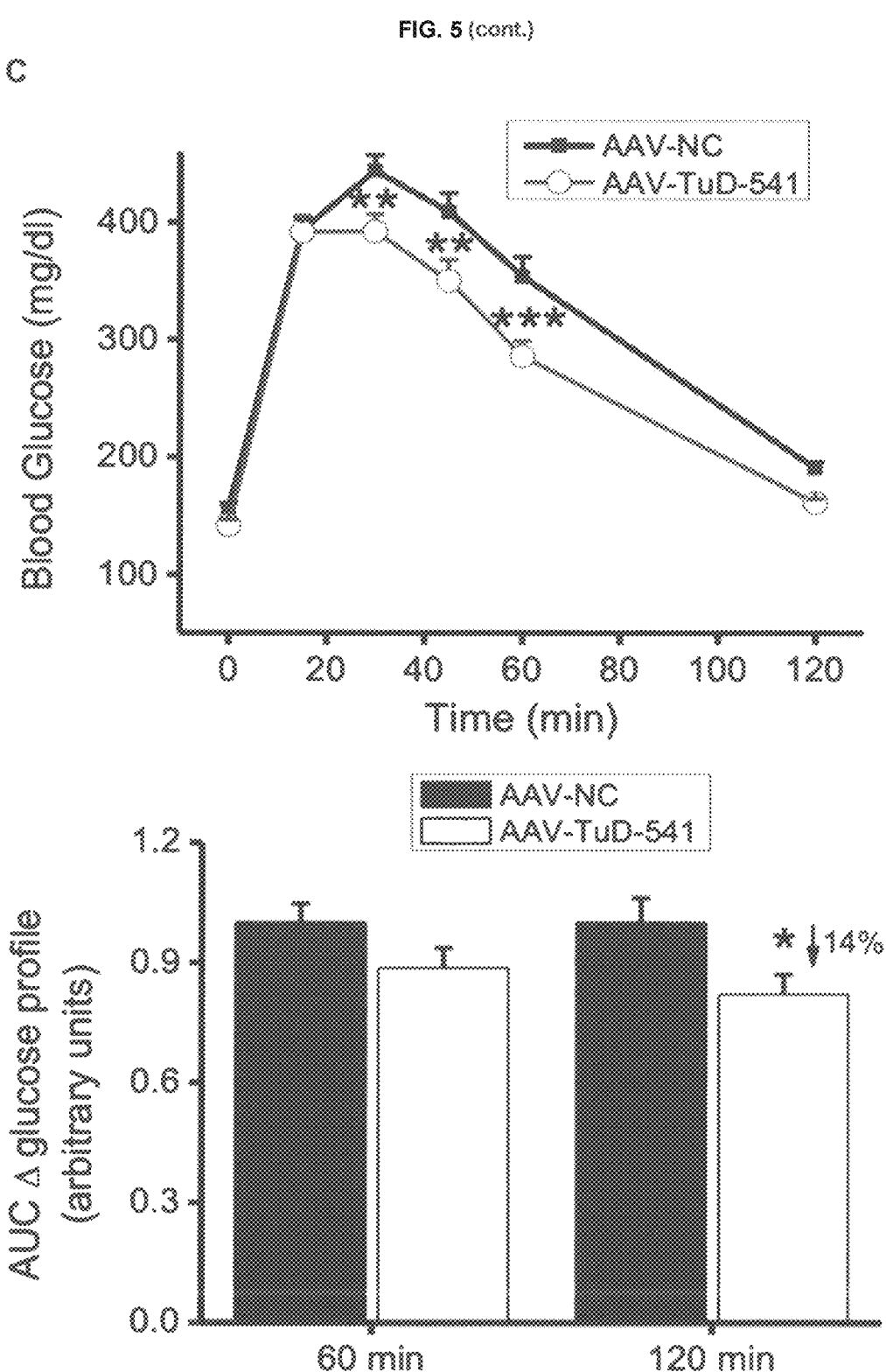

FIG. 5: Improvement in glucose tolerance following an intraperitoneal glucose load (ipGTT, 2 g glucose/kg) performed on week 4 of therapy in wild-type mice with combined hepatic-specific inhibition of miR-541 and miR-379 (FIG. 5A, same profile as presented in FIG. 4), hepatic-specific inhibition of miR-379 (FIG. 5B) or hepatic-specific inhibition of miR-541 activity (FIG. 5C) (AAV-TuD, open circles in the upper graph and white bars in the lower graph of each panel) as compared to negative control (AAV-NC, closed squares in the upper part and black bars in the lower part of each panel). The time-course glucose profile is presented in the upper graph, while the corresponding area under the curve is shown in the lower graph of each panel. A synergistic improvement in glucose clearance was observed in response to the combined inhibition of miR-541 and miR-379 activity.

Figure 6:
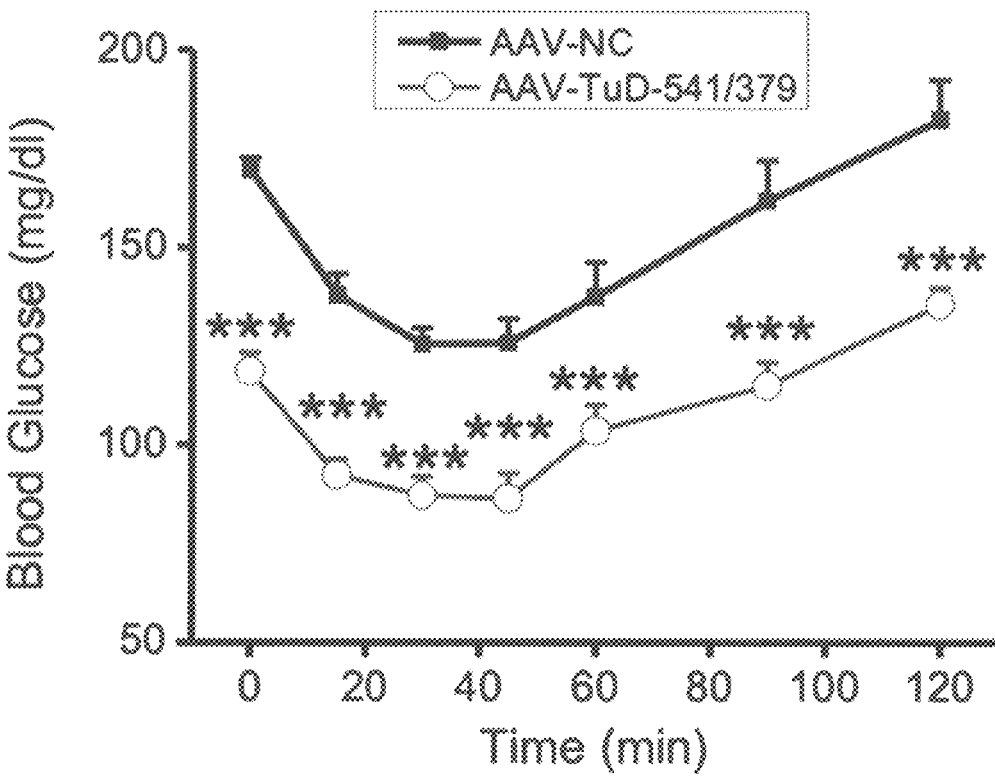
Figure 6:
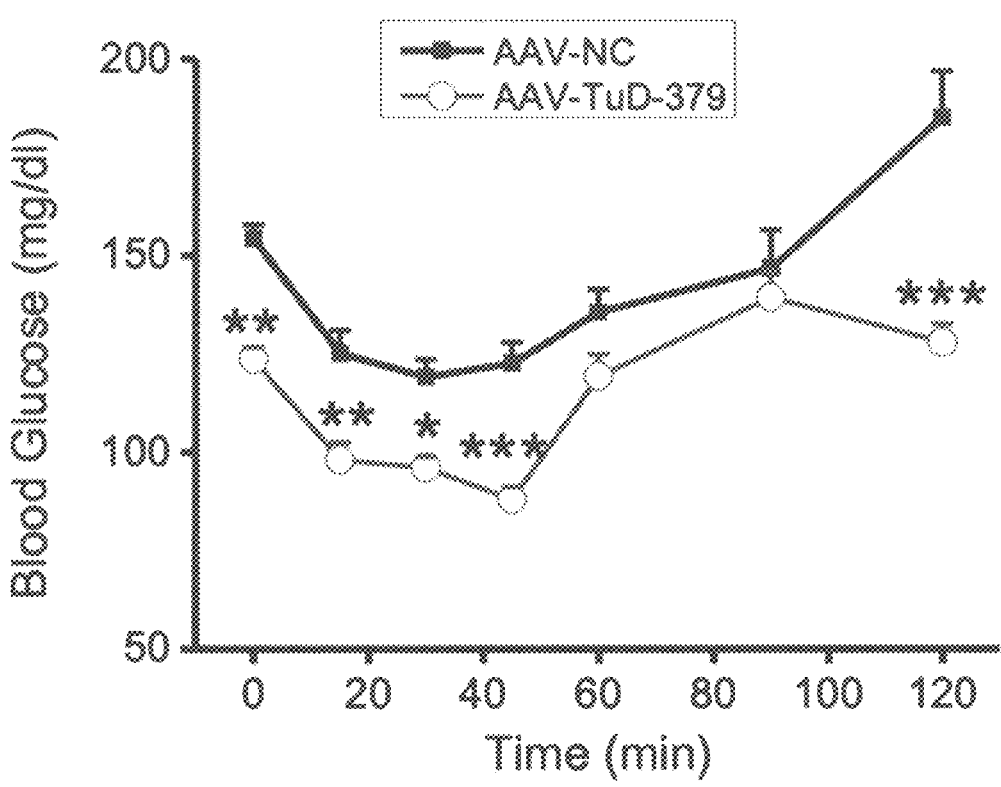
Figure 6:
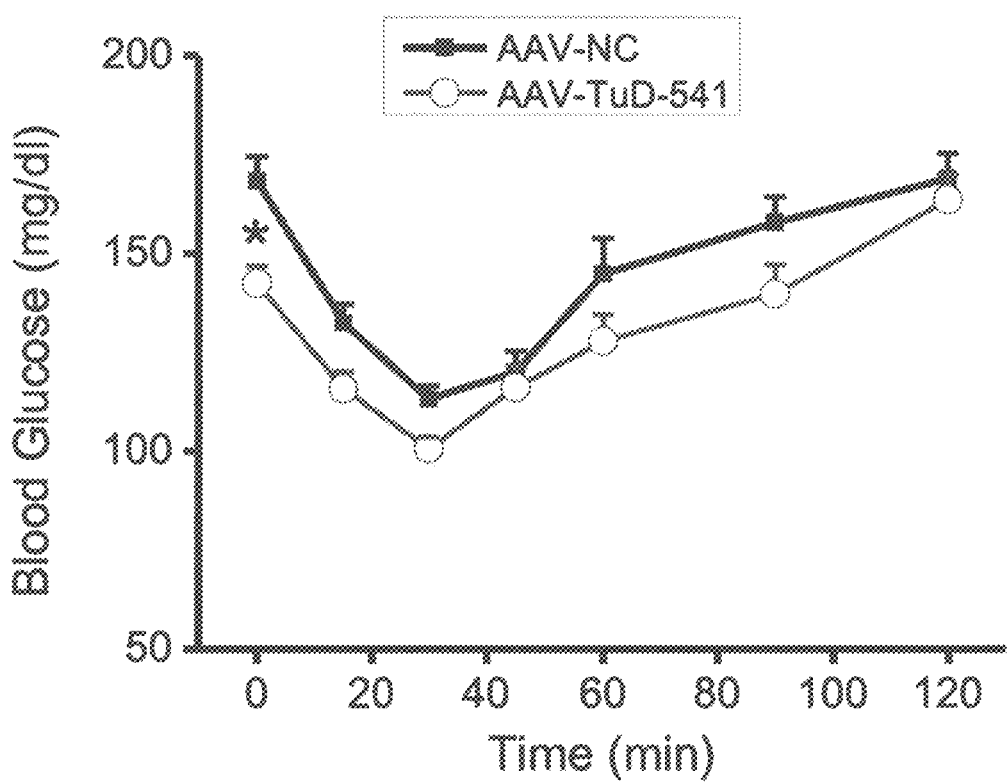

FIG. 6: Blood glucose levels in response to an exogenous insulin bolus (0.7 IU insulin/kg) intraperitoneally administered on week 3 of therapy to wild-type mice with combined hepatic-specific inhibition of miR-541 and miR-379 (FIG. 6A), hepatic-specific inhibition of miR-379 (FIG. 6B) or hepatic-specific inhibition of miR-541 activity (FIG. 6C) (AAV-TuD, open circles in each FIG. 6A-C) as compared to negative control (AAV-NC, closed squares in each FIG. 6A-C). Only in animals carrying hepatic-specific inhibition of both miR-541 and miR-379 activity, a significant reduction in glucose levels was found at all time points studied, as compared to negative control animals.

Figure 7:
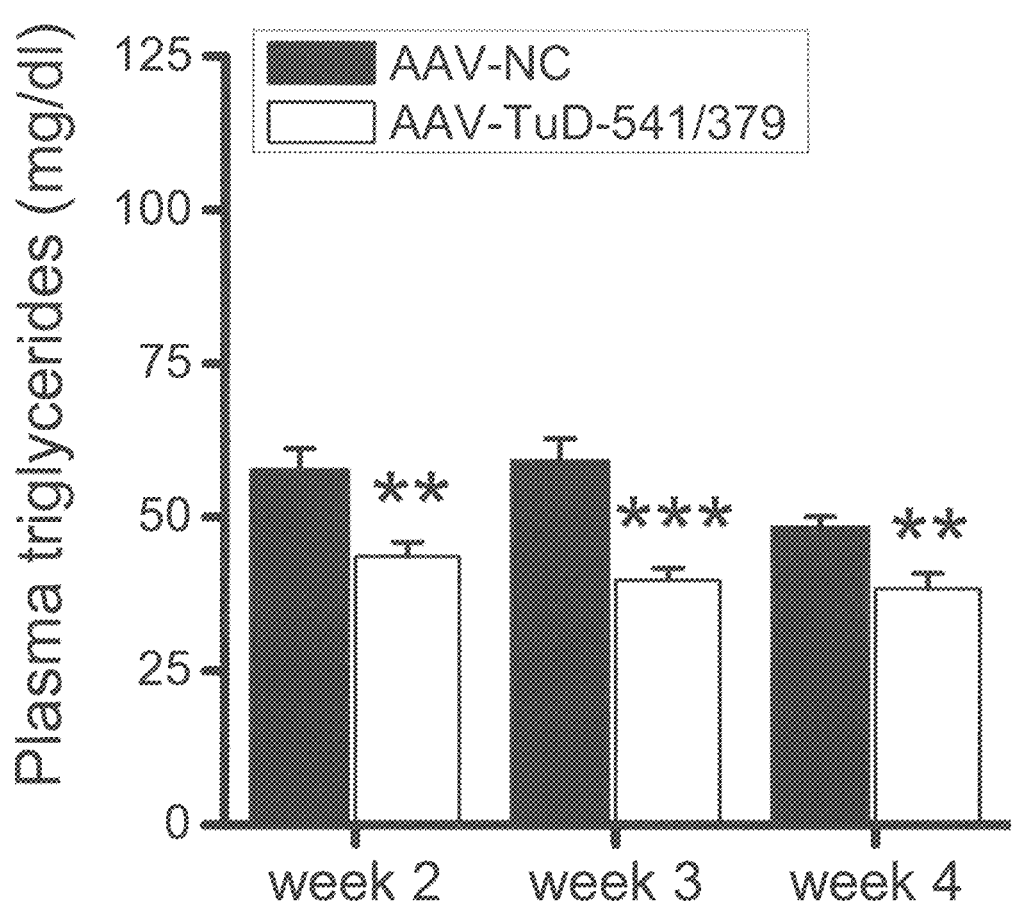
Figure 7:
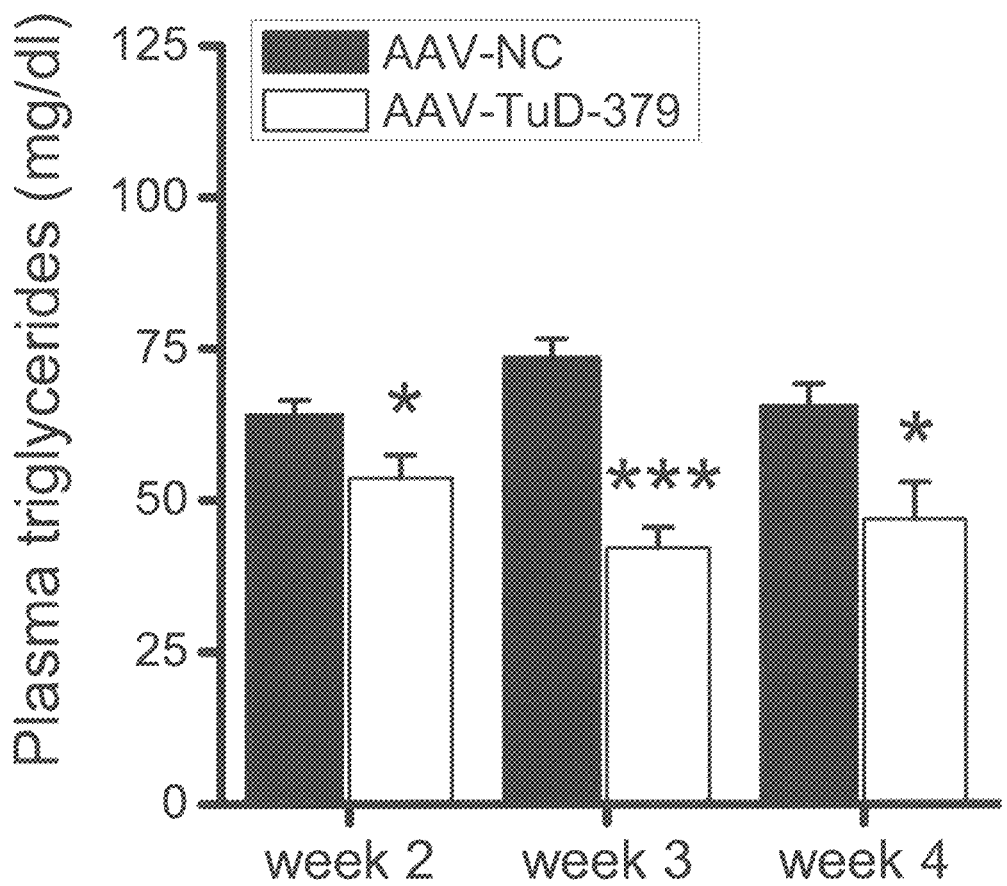
Figure 7:
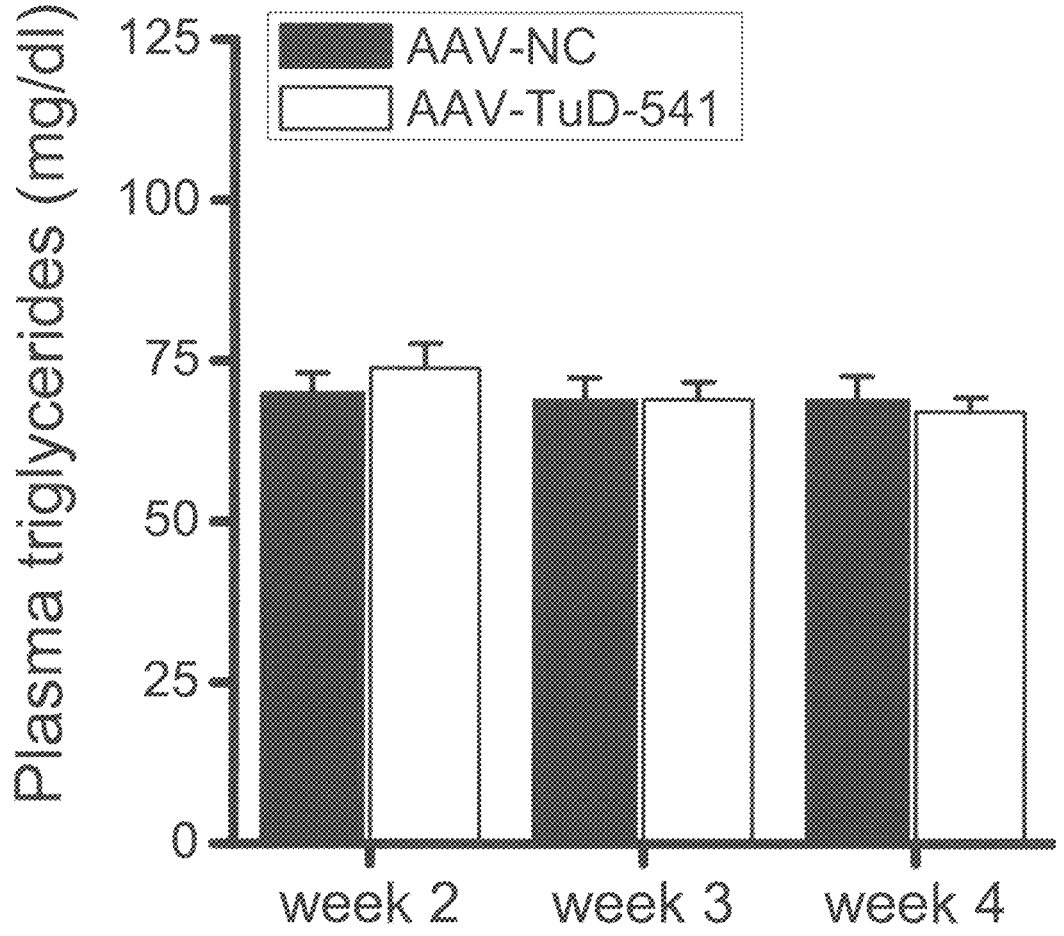

FIG. 7: Plasma triglyceride levels (5-6 h fasting) 2, 3 and 4 weeks after treatment in wild-type mice with combined hepatic-specific inhibition of miR-541 and miR-379 (FIG. 7A), hepatic-specific inhibition of miR-379 (FIG. 7B) and hepatic-specific inhibition of miR-541 activity (FIG. 7C) (AAV-TuD, white bars) as compared to negative control (AAV-NC, black bars). A robust lowering effect of circulating triglycerides was observed in response to the combined hepatic-specific inhibition of miR-541 and miR-379 activity.

The following sequences are provided herein:

```
RNA Mus musculus
miR-379-5p
bold: complementary sequence to inhibitor SEQ ID
NO: 3
                                      SEQ ID NO: 1
5'-UGGUAGACUAUGGAACGUAGG-3'

RNA Mus musculus
miR-541-5p
bold: complementary sequence to inhibitor SEQ ID
NO: 4
                                      SEQ ID NO: 2
5'-AAGGGAUUCUGAUGUUGGUCACACU-3'

DNA artificial
Inhibitor of miR-379
                                      SEQ ID NO: 3
5'-GTTCCATAGTCTACC-3'

DNA artificial
Inhibitor of miR-541
                                      SEQ ID NO: 4
5'-CAACATCAGAATCCCT-3'

RNA artificial
Inhibitory sequence to miR-379 and miR-541
comprised by TuD
```

-continued

```
                                      SEQ ID NO: 5
5'-GACGGCGCUA GGAUCAUCAA CAGUGUGACC AACAUCAUCU

AGAAUCCCUU CAAGUAUUCU GGUCACAGAA UACAACCCUA

CGUUCCAAUC UUAGUCUACC ACAAGAUGAU CCUAGCGCCG

UC-3'
```

The invention is further illustrated by the following examples, however, without being limited to the example or by any specific embodiment of the examples.

EXAMPLES

Levels of expression of different microRNAs belonging to the DIk1-Dio3 locus were determined by semiquantitative real-time PCR using TaqMan microRNA assays in liver biopsies from healthy volunteers (n=10) and obese subjects (n=37) who were not on diabetes medications. A consistent upregulation of the microRNAs examined (miR-127, miR-337, miR-379, miR-382, miR-134, miR-541, miR-409) was observed in the liver samples from obese subjects. The two microRNAs showing the highest increments in their expression were miR-379 and miR-541. Significant correlations between the levels of expression of these transcripts and different metabolic indicators were detected, as shown for miR-541 in Table 1.

The impact of hepatic miR-541 and miR-379 activity inhibition for metabolism was studied in vivo by the rAAV-delivery of tough decoy (TuD) inhibitors under the control of the hepatic-specific LP1 promoter. Generation of the construct delivered by the AAVs were carried out according to Rose A J et al. *Cell Metab* 2011, 14 (1): 123-30. Briefly, to clone these inhibitors into the construct delivered by the rAAV vector, the negative control sequence from the original vector was replaced by the tough decoy sequence using Bglll and Sall restriction enzymes. These inhibitor types were previously demonstrated to strongly inhibit the activity of their target microRNAs in vitro (unpublished observations). In three separate studies of the inventors of the present invention, C57BL/6J mice (12 animals per group) were administered with AAVs (5×1011 viral genomes per mouse) expressing a negative control sequence or the tough decoy inhibitor against both miR-541 and miR-379 (study 1, sequence according to SEQ ID NO: 5), a negative control sequence or the tough decoy inhibitor against miR-379 (study 2), and a negative control sequence or the tough decoy inhibitor against miR-541 (study 3). Body weight as well as food and water intake were monitored regularly, ipGTTs (2 g glucose/kg) were conducted 2 and 4 weeks after virus administration, while an ITT (0.7 IU/kg) was performed 3 weeks after the onset of the study, in both cases after fasting the animals for 6 h prior to the tests, which started between 14:00-15:00 h (a schematic representation of the experimental protocol is depicted in FIG. 1). In addition, postprandial blood samples were collected at 23:00 h on weeks 2.5 and 4.5. The experiments were terminated 5 weeks after the administration of the viral vectors, half of the animals (n=6 mice per group) were killed at 14:00 h after a 5-6 h fasting, while the other half were killed at 23:00 h during the postprandial state. In study 1, no differences on body weight, food or water intake were detected between the animals receiving the negative control sequence and the animals carrying the combined hepatic-specific inhibition of miR-541 and miR-379 activity (AAV-TuD). Fasting glucose was significantly lower in the AAV-TuD group from week 2 till the end of the study, while fasting insulin concentrations were significantly reduced from week 3, and hepatic insulin resistance, as estimated by the homeostatic model assessment (HOMA-IR) index, which is calculated from fasting plasma insulin (FPI) and fasting plasma glucose (FPG) concentrations [FPI (mU/l)×FPG (mmol/l)/22.5], was found to be significantly lower in the AAV-TuD group from week 2 till termination (FIG. 2). In addition, plasma triglyceride levels were also significantly reduced in this group irrespectively of the feeding conditions of the animals (FIGS. 3 and 7A). Glucose clearance was also significantly better in the AAV-TuD group (60% improvement in week 4, $p<0.001$; FIGS. 4A, 4B and 5A). Despite a significant improvement in glucose clearance was also observed in the animals receiving the other two tough decoy inhibitors tested, the effect was less pronounced (14% and 36% improvement in response to the single tough decoys against miR-379, FIG. 5B, and miR-541 activity, FIG. 5C, respectively), indicating a synergistic effect in response to the simultaneous inhibition of both microRNAs. Moreover, the combined inhibition of both microRNAs also induced a remarkable potentiation of the glucose-lowering effect in response to an exogenous bolus of insulin, with significantly ($p<0.001$) reduced glucose levels as compared to negative control that were sustained over a two hour period (FIG. 6A). Again, this effect was not matched by the single inhibition of either of the two microRNAs (FIGS. 6B and 6C). Blood glucose levels were determined by glucose meter (Accu-Check). Triglyceride levels were measured by enzymatic assay (Sigma-Aldrich), while insulin levels were quantified by ELISA (Alpco). The area under the curve of the glucose profile in response to an intraperitoneal glucose load (2 g/kg) was used for the calculation of the improvement in glucose clearance.

TABLE 1 shows the correlation between hepatic levels of expression of miR-541 and different metabolic parameters in healthy volunteers and obese subjects who are not on diabetes medications.

| miR-541 vs. insulin | miR-541 vs. HOMA-IR | miR-541 vs. triglycerides | miR-541 vs. ASAT | miR-541 vs. bilirubin | miR-541 vs. leptin | miR-541 vs. HDL |
|---|---|---|---|---|---|---|
| r = 0.5495 p = 0.0275 | r = 0.5353 p = 0.0326 | r = 0.6975 p = 0.0038 | r = 0.5485 p = 0.0278 | r = 0.6469 p = 0.0068 | r = 0.7427 p = 0.0010 | r = −0.4721 ns |

The invention is further characterized by the following items:

1. A composition comprising
   (a) an inhibitor of miR-379 or a portion or fragment thereof and an inhibitor of miR-541 or a portion or fragment thereof, and/or
   (b) an inhibitor of the target site of miR-379 or a portion or fragment thereof and an inhibitor of the target site of miR-541 or a portion or fragment thereof, and/or
   (c) a combination of an inhibitor of miR-379 or a portion or fragment thereof and an inhibitor of the target site of miR-541 or a portion or fragment thereof or a combination of an inhibitor of the target site of miR-379 or a portion or fragment thereof and an inhibitor of miR-541 or a portion or fragment thereof.

2. The composition of item 1, wherein at least one inhibitor of miR-379 or a portion or fragment thereof comprises a nucleotide sequence complementary to or hybridizing to miR-379 or a portion or fragment thereof, and at least one inhibitor of miR-541 or a portion or fragment thereof comprises a nucleotide sequence complementary to or hybridizing to miR-541 or a portion or fragment thereof.

3. The composition of item 1 or 2, wherein a portion of miR-379 has a nucleotide sequence according to SEQ ID NO: 1, wherein not more than 6 nucleotides are substituted, and a portion of miR-541 has a nucleotide sequence according to SEQ ID NO: 2, wherein not more than 8 nucleotides are substituted.

4. The composition of any one of items 1 to 3, wherein at least one inhibitor comprises a nucleic acid sequence comprising at least 10 nucleotides.

5. The composition of any one of items 1 to 4, wherein at least one inhibitor is selected from the group consisting of Tough Decoys (TuD), Decoys, antisense oligonucleotides, anti-miR, block-miR, ribozymes, external guide sequence (EGS), oligonucleotides, small interference RNA (siRNA), small temporal RNA (stRNA), short hairpin RNA (shRNA), small RNA-induced gene activation (RNAa), small activating RNA (saRNA), locked nucleic acids (LNA), antagomirs, and peptide nucleic acids (PNA).

6. The composition of item 5, wherein at least one inhibitor is a Tough Decoy RNA (TuD).

7. The composition of any one of items 1 to 6, wherein at least one inhibitor comprises a chemical modification of the nucleic acid sequence selected from the group consisting of nucleic acid analogs comprising N-acetyl-galactosamine (GalNAc), phosphorothioate DNA (PS), 2'-O-methyl RNA (OMe), 2'-O-methoxy-ethyl RNA (MOE), peptide nucleic acid (PNA), N3'-P5'-phosphoroamidate (NP), 2'-fluoro-arabino nucleic acid (FANA), morpholino phosphoroamidate (MF), cyclohexene nucleic acid (CeNA), and tricycleDNA (tc-DNA).

8. The composition of any one of items 1 to 7, wherein at least one inhibitor is comprised by a delivery vehicle selected from the group consisting of adeno-associated virus (AAV), lentiviral vector, polyethylene imine (PEI), cationic liposomes, silica nanoparticles, PEGylated PLGA, and neutral lipid.

9. The composition of any one of items 1 to 8, wherein at least one inhibitor is comprised by an adeno-associated virus (AAV).

10. The composition of any one of items 1 to 9, wherein the inhibitor of miR-379 or a portion or fragment thereof comprises a nucleotide sequence of SEQ ID NO: 3, wherein not more than 5 nucleotides are substituted, and/or the inhibitor of miR-541 or a portion or fragment thereof comprises a nucleotide sequence of SEQ ID NO: 4, wherein not more than 5 nucleotides are substituted.

11. The composition of any one of items 1 to 10, comprising an inhibitor of miR-379 or a portion or fragment thereof and an inhibitor of miR-541 or a portion or fragment thereof on the same molecule, wherein said molecule comprises a nucleotide sequence complementary to or hybridizing to miR-379 or a portion or fragment thereof and a nucleotide sequence complementary to or hybridizing to miR-541 or a portion or fragment thereof.

12. The composition of item 11, wherein said inhibitor comprises the nucleotide sequence of SEQ ID NO: 5, wherein not more than 10 nucleotides are substituted.

13. The composition of any one of items 1 to 12, which is a pharmaceutical composition.

14. The composition of any one of items 1 to 13 for use in treating or preventing a metabolic disease, a disease related to a metabolic disorder, and/or cancer.

15. The composition of item 14, wherein said metabolic disease or disease related to a metabolic disorder is selected from the group consisting of glucocorticoid hormone driven metabolic dysfunction, obesity, diabetes, diabesity, metabolic syndrome, insulin resistance, hyperglycemia, (systemic) dyslipidemia, Cushing's syndrome, adverse or side effects associated with or caused by glucocorticoid (GC) treatment or excess, atherosclerosis, heart disease, stroke, (cancer) cachexia, growth defects, hepatic steatosis, NASH, and liver fibrosis.

The invention claimed is:

1. A composition comprising an inhibitor of miR-379 and an inhibitor of miR-541, wherein miR-379 has the nucleotide sequence of SEQ ID NO: 1, and miR-541 has the nucleotide sequence of SEQ ID NO: 2 or SEQ ID NO: 6, wherein the inhibitor of miR-379 comprises a nucleotide sequence of at least 15 nucleotides in length that is complementary to, and hybridizes to, miR-379, and wherein the inhibitor of miR-541 comprises a nucleotide sequence of at least 15 nucleotides in length that is complementary to, and hybridizes to, miR-541, wherein at least one of the inhibitors comprises a chemical modification of the nucleic acid sequence selected from the group consisting of nucleic acid analogs comprising N-acetylgalactosamine (GalNAc), phosphorothioate DNA (PS), 2'-O-methyl RNA (OMe), 2'-O-methoxy-ethyl RNA (MOE), peptide nucleic acid (PNA), N3'-P5'-phosphoroamidate (NP), 2'-fluoro-arabino nucleic acid (FANA), morpholino phosphoroamidate (MF), cyclohexene nucleic acid (CeNA), and tricycleDNA (tc-DNA), and wherein at least one of the inhibitors is a Tough Decoy RNA (TuD).

2. A composition comprising an inhibitor of miR-379 and an inhibitor of miR-541, wherein miR-379 has the nucleotide sequence of SEQ ID NO: 1, and miR-541 has the nucleotide sequence of SEQ ID NO: 2 or SEQ ID NO: 6, wherein the inhibitor of miR-379 comprises a nucleotide sequence of at least 15 nucleotides in length that is complementary to, and hybridizes to, miR-379, and wherein the inhibitor of miR-541 comprises a nucleotide sequence of at least 15 nucleotides in length that is complementary to, and hybridizes to, miR-541, wherein at least one of the inhibitors comprises a chemical modification of the nucleic acid sequence selected from the group consisting of nucleic acid analogs comprising N-acetylgalactosamine (GalNAc), phosphorothioate DNA (PS), 2'-O-methyl RNA (OMe), 2'-O-methoxy-ethyl RNA (MOE), peptide nucleic acid (PNA), N3'-P5'-phosphoroamidate (NP), 2'-fluoro-arabino nucleic acid (FANA), morpholino phosphoroamidate (MF), cyclohexene nucleic acid (CeNA), and tricycleDNA (tc-DNA), and wherein at least one of the inhibitors is comprised by a delivery vehicle selected from the group consisting of polyethylene imine (PEI), cationic liposomes, silica nanoparticles, PEGylated PLGA, and neutral lipid.

3. The composition of claim 1 or 2, wherein the inhibitor of miR-379 comprises the nucleotide sequence of SEQ ID NO: 3, and/or the inhibitor of miR-541 comprises the nucleotide sequence of SEQ ID NO: 4 or SEQ ID NO: 7.

4. The composition of claim 1 or 2, comprising the inhibitor of miR-379 and the inhibitor of miR-541 on the same molecule, wherein said molecule comprises a nucleotide sequence that is complementary to, and hybridizes to, miR-379 and a nucleotide sequence that is complementary to, and hybridizes to, miR-541.

5. A molecule comprising the nucleotide sequence of SEQ ID NO: 5.

6. A molecule comprising the nucleotide sequence of SEQ ID NO: 8.

7. A pharmaceutical composition comprising (i) the composition of claim 1 or 2 and (ii) a vehicle or carrier.

8. A pharmaceutical composition comprising (i) the molecule of claim 5 or 6 and (ii) a vehicle or carrier.

\* \* \* \* \*

SEQUENCE LISTING

```
<160> NUMBER OF SEQ ID NOS: 8

<210> SEQ ID NO 1
<211> LENGTH: 21
<212> TYPE: RNA
<213> ORGANISM: Mus musculus

<400> SEQUENCE: 1
ugguagacua uggaacguag g                                            21

<210> SEQ ID NO 2
<211> LENGTH: 25
<212> TYPE: RNA
<213> ORGANISM: Mus musculus

<400> SEQUENCE: 2
aagggauucu gauguugguc acacu                                        25

<210> SEQ ID NO 3
<211> LENGTH: 15
<212> TYPE: DNA
<213> ORGANISM: Artificial Sequence
<220> FEATURE:
<223> OTHER INFORMATION: Artificially Synthesized

<400> SEQUENCE: 3
gttccatagt ctacc                                                   15

<210> SEQ ID NO 4
<211> LENGTH: 16
<212> TYPE: DNA
<213> ORGANISM: Artificial Sequence
<220> FEATURE:
<223> OTHER INFORMATION: Artificially Synthesized

<400> SEQUENCE: 4
caacatcaga atccct                                                  16

<210> SEQ ID NO 5
<211> LENGTH: 122
<212> TYPE: RNA
<213> ORGANISM: Artificial Sequence
<220> FEATURE:
<223> OTHER INFORMATION: Artificially Synthesized

<400> SEQUENCE: 5
gacggcgcua ggaucaucaa cagugugacc aacaucaucu agaaucccuu caaguauucu      60
ggucacagaa uacaacccua cguuccaauc uuagucuacc acaagaugau ccuagcgccg     120
```

-continued

```
uc                                                                        122

<210> SEQ ID NO 6
<211> LENGTH: 25
<212> TYPE: RNA
<213> ORGANISM: Homo sapiens

<400> SEQUENCE: 6
aaaggauucu gcugucgguc ccacu                                               25

<210> SEQ ID NO 7
<211> LENGTH: 16
<212> TYPE: DNA
<213> ORGANISM: Artificial Sequence
<220> FEATURE:
<223> OTHER INFORMATION: Artificially Synthesized

<400> SEQUENCE: 7
cgacagcaga atcctt                                                         16

<210> SEQ ID NO 8
<211> LENGTH: 122
<212> TYPE: RNA
<213> ORGANISM: Artificial Sequence
<220> FEATURE:
<223> OTHER INFORMATION: Artificially Synthesized

<400> SEQUENCE: 8
gacggcgcua ggaucaucaa caguggggacc gacagcaucu agaauccuuu caaguauucu        60
ggucacagaa uacaacccua cguuccaauc uuagucuacc acaagaugau ccuagcgccg         120
uc                                                                        122
```